(12) United States Patent
Maeda et al.

(10) Patent No.: US 6,621,571 B1
(45) Date of Patent: Sep. 16, 2003

(54) METHOD AND APPARATUS FOR INSPECTING DEFECTS IN A PATTERNED SPECIMEN

(75) Inventors: Shunji Maeda, Yokohama (JP); Atsushi Yoshida, Toyohashi (JP); Yukihiro Shibata, Fujisawa (JP); Toshihiko Nakata, Hiratsuka (JP); Hiroaki Shishido, Yokohama (JP); Minoru Yoshida, Yokohama (JP); Sachio Uto, Yokohama (JP)

(73) Assignee: Hitachi, Ltd., Tokyo (JP)

( * ) Notice: Subject to any disclaimer, the term of this patent is extended or adjusted under 35 U.S.C. 154(b) by 323 days.

(21) Appl. No.: 09/698,167

(22) Filed: Oct. 30, 2000

(30) Foreign Application Priority Data

Oct. 29, 1999 (JP) ............................................ 11-307985

(51) Int. Cl.[7] .............................................. G01N 21/88
(52) U.S. Cl. ................................. 356/237.5; 356/237.4
(58) Field of Search ................ 356/237.1, 237.2–237.6, 356/239.7, 239.8, 600, 243.7, 394; 250/559.44

(56) References Cited

U.S. PATENT DOCUMENTS

| | | | |
|---|---|---|---|
| 5,652,657 A | * | 7/1997 | Yoshii et al. ................. 356/394 |
| 6,031,607 A | * | 2/2000 | Miyazaki .................. 356/237.1 |
| 6,084,716 A | * | 7/2000 | Sanada et al. ............... 359/629 |
| 6,091,488 A | * | 7/2000 | Bishop ..................... 356/237.5 |

FOREIGN PATENT DOCUMENTS

| | | |
|---|---|---|
| JP | 07318326 | 12/1995 |
| JP | 08320294 | 12/1996 |
| JP | 10078668 | 3/1998 |
| JP | 11072905 | 3/1999 |

OTHER PUBLICATIONS

Dingel, et al., Speckle Reduction with Virtual Incoherent Laser Illumination Using a Modified Fiber Array, Optik, vol. 94, No. 3, p. 132–6 (Sep. 1993).*

* cited by examiner

Primary Examiner—Michael P. Stafira
Assistant Examiner—Vincent P. Barth
(74) Attorney, Agent, or Firm—Antonelli, Terry, Stout & Kraus, LLP

(57) ABSTRACT

In a method and apparatus for detecting pattern defects, a UV laser is focused on a pupil of an objective lens and scanned; the focused and scanned UV lens illuminates a specimen on which patterns are formed; the specimen illuminated by the UV laser is imaged: and the resulting image of the specimen is compared with a previously stored reference image. The specimen illuminated by UV light is imaged using an anti-blooming time delay integration image sensor or a back-illumination time delay integration image sensor; and the resulting specimen image is compared with a previously stored reference image.

30 Claims, 27 Drawing Sheets

AS                              FS

AS                    FS

FIG.6
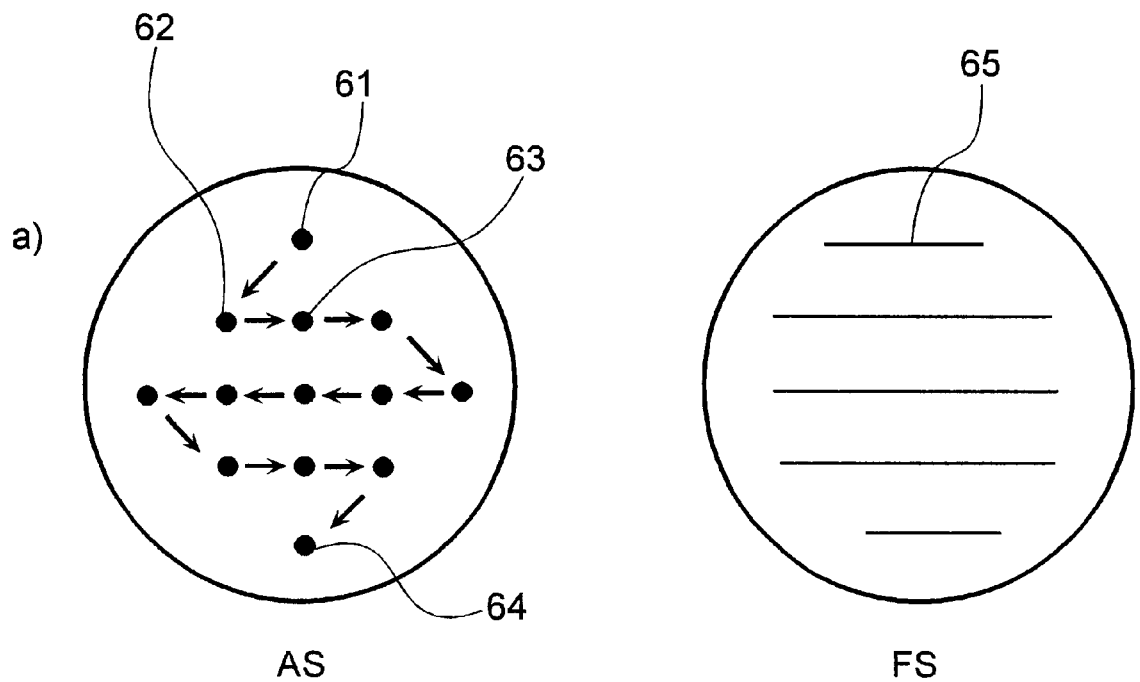
a)
AS  FS
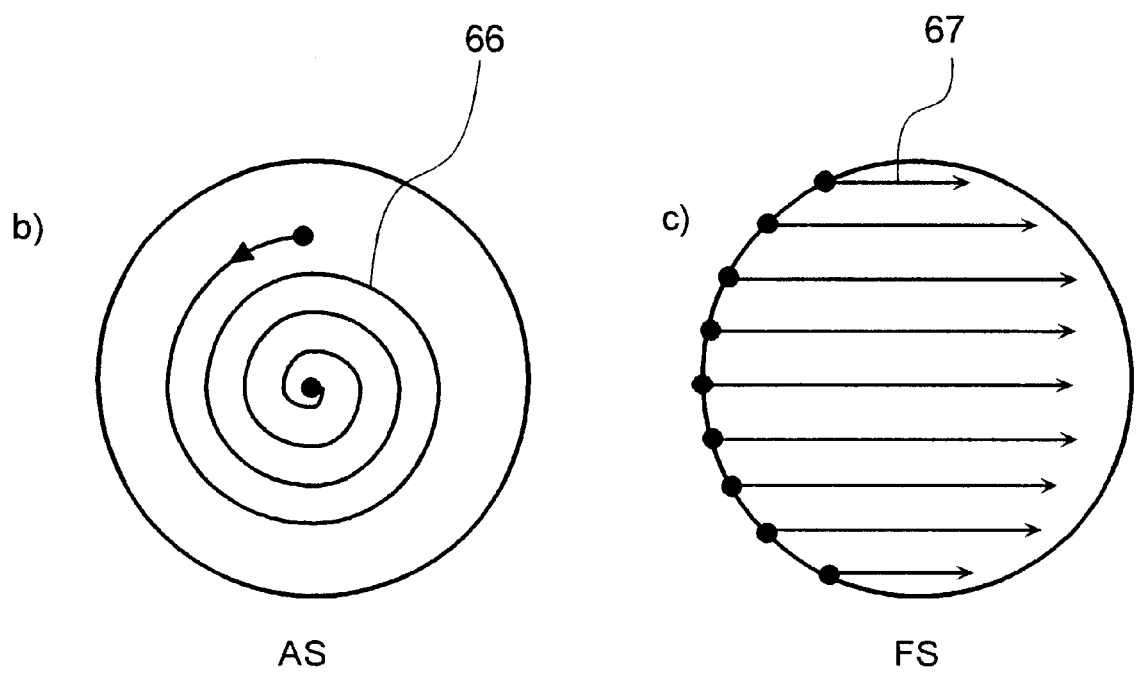
b) AS
c) FS

FS a)

b)

(TDI : Time Delay & Integration)

- An approximation line is determined for each area centered around a focus point on the distribution diagram.
  The gain and offset of the approximation line are used as correction cefficents.

- The area size can be varied according to the frequency in the distribution diagram.

FIG.35
1) After pixel alignment
| slope | intercept |
|-------|-----------|
| 0.705 | 55.947 |
$Vr = 447.4806$
$Ve = 40.02821$
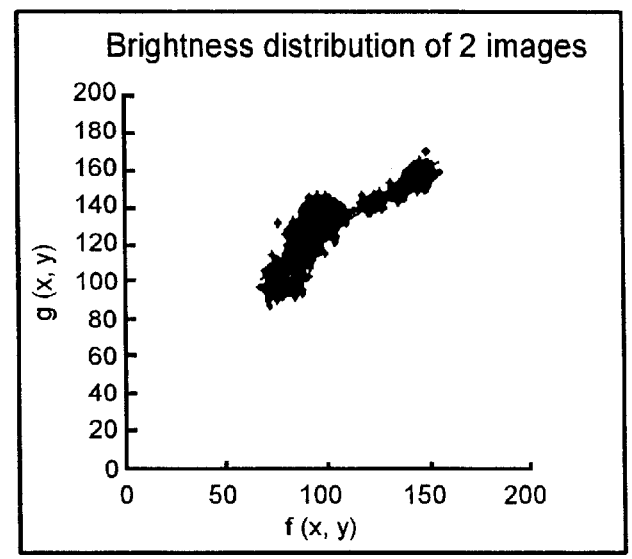
2) After Brightness matching
| slope | intercept |
|-------|-----------|
| 0.986 | 2.567 |
$Vr = 478.921$
$Ve = 8.598012$
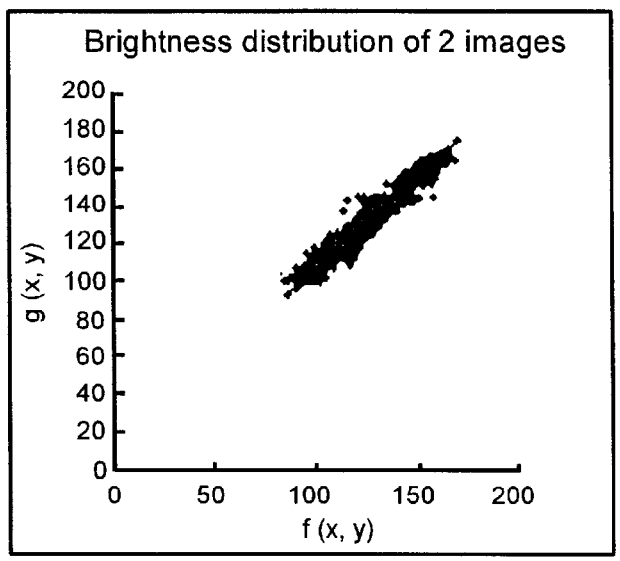

| defect number | defect coordinates | defect area | defect length | defect brightness difference | defect reliability (frequency information) |
|---|---|---|---|---|---|
| 1 | (100.10, 202.20) | 4.54 | (2.2, 1.5) | 14 | 100 |
| 2 | (120.75, 232.72) | 10.2 | (2.9, 4.2) | 20 | 250 |
| 3 | . . . . . . . . . . . . . | | | | |

(b)

| defect number | defect coordinates | defect area | defect length | defect brightness difference | defect reliability (distance information) |
|---|---|---|---|---|---|
| 1 | (100.10, 202.20) | 4.54 | (2.2, 1.5) | 14 | 25 |
| 2 | (120.75, 232.72) | 10.2 | (2.9, 4.2) | 20 | 12 |
| 3 | . . . . . . . . . . . . . | | | | |

(c)

| defect number | defect coordinates | defect area | defect length | defect brightness difference | defect reliability (position information) |
|---|---|---|---|---|---|
| 1 | (100.10, 202.20) | 4.54 | (2.2, 1.5) | 14 | (100, 200) |
| 2 | (120.75, 232.72) | 10.2 | (2.9, 4.2) | 20 | (250, 200) |
| 3 | . . . . . . . . . . . . . | | | | | form
METHOD AND APPARATUS FOR INSPECTING DEFECTS IN A PATTERNED SPECIMEN

BACKGROUND OF THE INVENTION

The present invention relates to a defect inspection method and apparatus to be same used for inspection of patterns and contaminants in which an inspected pattern is examined for defects (short-circuits and line breaks), especially in semiconductor wafers, liquid crystal displays, and photomasks. In the following description, defects will be considered to include contaminants.

Conventionally, as described in Japanese laid-open patent publication number Hei 7-318326 (background technology 1), in this type of inspection device, the inspected pattern is moved while using an imaging element such as a line sensor, to detect an image of the inspected pattern. The detected image signal is compared to the concentrations in an image signal delayed by a predetermined interval, and discrepancies are recognized as defects.

Another conventional technology relating to defect inspection of inspected patterns is presented in Japanese laid-open patent publication number Hei 8-320294 (background technology 2). In this background technology 2, the inspected pattern is a semiconductor wafer or the like in which a chip contains both areas with high pattern densities, such as memory arrays, and areas with low pattern densities, such as peripheral circuitry. The frequency distribution of the brightness of the detected image is used to apply tone conversion to the digital image signal obtained from AID conversion of the detected image signal. This tone conversion is performed so that there is a predetermined relationship between the brightnesses or contrasts of the high-density areas and the low-density areas on the inspected pattern. This tone-converted image signal is aligned with an image signal that has been tone converted for comparison. The two images are compared to perform high-precision inspection of fine defects.

Furthermore, a device for inspecting photomask patterns is presented in Japanese laid-open patent publication number Hei 10-78668 (background technology 3). In this device, a UV laser, such as an excimer laser, is used as a light source. A diffuser panel inserted in the light path is rotated to reduce the coherence of the UV light, allowing a uniform UV illumination to be applied to the mask. Characteristics are calculated from the resulting mask image data, and these characteristics are used to evaluate the quality of the photomask.

In recent years, LSI production has involved higher degrees of fineness in the circuit patterns formed on wafers to respond to the demand for higher densities of integration. Pattern widths of 0.25 microns and less are being used, reaching the limits of the resolutions provided by imaging optical systems. For this reason, the use of high-NA imaging optical systems and super-resolution technology is being developed.

However, high-NA imaging has reached physical limitations. Thus, the essential approach involves shortening the wavelength used for detection from UV to DUV.

Also, since inspection must be performed at high speeds, it is not possible to have a tightly focused laser beam scanning the specimen. If, on the other hand, a laser beam is spread out to cover the entire viewing area, specking will take place. There will also be over-shooting and under-shooting, known as linking, at the edges of the circuit pattern. These issues prevent good images from being obtained.

SUMMARY OF INVENTION

The object of the present invention is to overcome the problems described above and to provide a defect inspecting method and apparatus that performs high-speed, high-resolution detection of fine circuit patterns.

In order to achieve this object, the present invention uses a light source that emits UV light as the light source for the inspecting device. More specifically, in the embodiments of the present invention, a UV laser light source is used as the light source. Means for restricting speckling of the UV laser is disposed in the optical path. Coherence of the UV light is reduced and the UV light is illuminated on the surface of the inspected item so that an image of the inspected item can be detected. UV light in this case can include DUV light.

In accordance with the present invention, this means for restricting speckling in the UV light can involve: 1) focusing the light from the light source onto one or multiple points on the pupil of the objective lens, and scanning the focused points over the pupil with a timing based on the storage time of the detector; 2) projecting the UV light emitted from the laser light source into a bundle of optical fibers with optical axis offsets and focusing the exiting lights onto the pupil of the objective lens; 3) projecting the light into a set of optical fibers having optical path lengths at or greater than the coherence length of the laser light source, and focusing the exiting light onto the pupil of the objective lens; 4) providing a diffuser panel and moving it relative to the light beam in a direction-roughly perpendicular to the optical axis; 5) illuminating the pupil using a combination of the above methods; and the like.

Also, in order to enhance pattern contrast, the ability to freely control the polarization of the laser was studied. By controlling the orientation of the polarization and ellipticity of the illuminating light, partial polarized components in the detected light can be detected.

In order to achieve the objects described above, the present invention provides a pattern defect inspecting device including: laser light source means emitting a laser beam; means for reducing coherence of the laser beam emitted by the laser light source means; means for illuminating a specimen with a laser beam having coherence reduced by the coherence reducing means; means for detecting an image of the specimen illuminated by the laser beam produced from the illuminating means; and means for detecting pattern defects formed on the specimen based on information relating to the image of the specimen detected by the image detecting means.

In order to achieve the objects described above, another aspect of the present invention provides a pattern defect inspecting device including: laser light source means emitting a UV laser beam; means for reducing coherence of the UV laser beam emitted by laser light source means; means for illuminating a specimen with a UV laser beam having its coherence reduced by the coherence reducing means; means for changing polarization of the UV laser beam; means for detecting an image of the specimen illuminated by the UV laser beam provided from the illuminating means and polarized by the polarizing means; and means for detecting pattern defects formed on the specimen based on information relating to the image of the specimen detected by the image detecting means. In order to achieve the objects described above, another aspect of the present invention provides a pat tern defect inspecting device including: laser light source means emitting a laser beam; means for reducing coherence of the laser beam emitted by laser light source means; means for illuminating a specimen with a laser beam having its coherence reduced by the coherence reducing means; means for detecting an image of the specimen illuminated by the laser beam produced from the illuminating means; and means for processing an image of the specimen detected by the image detecting means. A wafer with a diameter on the order of 200 mm is processed at a speed corresponding to a throughput of three units per hour, and defects of 100 nm can be detected on the patterns formed on the specimen.

In order to achieve the objects described above, another aspect of the present invention provides a pattern defect inspecting method including the steps of: illuminating with al UV laser a specimen on which a pattern is formed; imaging the specimen illuminated with the UV laser; and detecting defects on the pattern by comparing an image of the specimen obtained by the imaging step with a previously stored reference image.

In order to achieve the objects described above, another aspect of the present invention provides a pattern defect inspecting method including the steps of: focusing and scanning a UV laser beam on a pupil of an objective lens; illuminating a specimen on which a pattern is formed with the focused and scanned UV laser beam; imaging the specimen illuminated by the UV laser beam; and detecting defects on the pattern by comparing an image of the specimen obtained by the imaging step with a previously stored reference image.

In order to achieve the objects described above, another aspect of the present invention provides a pattern defect inspecting method including the steps of illuminating a specimen on which a pattern is formed with UV light; imaging the specimen illuminated by UV light; correcting image brightness for an image of the specimen obtained by the imaging step and a previously stored reference image so that the brightnesses are roughly identical; and detecting defects on the pattern by comparing the image of the specimen and the reference image which have been corrected for brightness.

In order to achieve the objects described above, another aspect of the present invention provides a pattern defect inspecting method including the steps of: reducing the coherence of a laser beam emitted from a laser light source; illuminating a surface of a specimen on which a pattern is formed via an objective lens using the laser beam with reduced coherence while varying the direction of illumination over time; imaging the specimen illuminated by the laser beam; and detecting defects on the pattern by comparing the image of the specimen obtained in the imaging step and a previously stored reference image.

In order to achieve the objects described above, another aspect of the present invention provides a pattern defect inspecting method including the steps of: illuminating a surface of a specimen using UV light; obtaining an image signal by imaging the surface of the specimen illuminated by the UV light; detecting defects of 100 nm and less on the specimen by processing the image signal; and outputting information relating to positions on the specimen of detected defects of 100 nm and less.

In order to achieve the objects described above, another aspect of the present invention provides a pattern defect inspecting method including the steps of: illuminating UV light on a wafer with a diameter that is at least on the order of 200 mm; detecting an image of the wafer by imaging the wafer illuminated by the UV light; detecting defects 100 nm and less on patterns formed on the wafer by processing the detected images of the wafer illuminated by the UV light, the detection being performed at a throughput of at least three wafers with 200 mm diameter per hour.

These and other objects, features and advantages of the invention will be apparent from the following more particular description of preferred embodiments of the invention, as illustrated in the accompanying drawings.

BRIEF DESCRIPTION OF THE DRAWINGS

FIG. 4($b$) is a diagram showing the illumination on the field of view; FIG. 4($c$) a pattern in the field of view; and FIG. 4($d$) shows a detection signal therefrom.

FIGS. 6($a$) to 6($d$) are diagrams showing two examples of the illumination from laser illumination according to the present invention on the pupil of a detection/objective lens and on the field of view.

FIGS. 35(a) and 35(b) are diagrams which illustrate examples of scatter diagrams according to the present invention.

FIGS. 36(a) to 36(c) are tables which illustrate defect output according to the present invention.

DESCRIPTION OF THE PREFERRED EMBODIMENT

Figure 1:
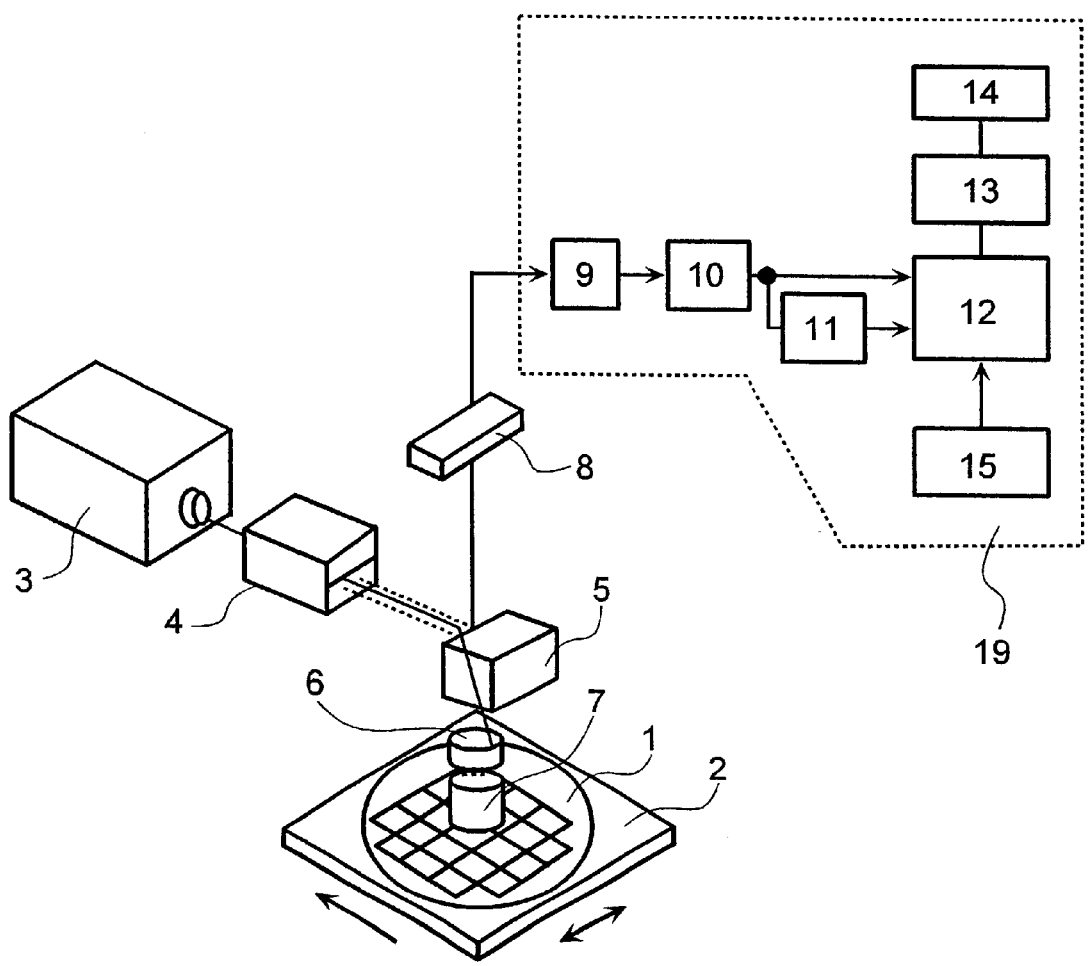
FIG. 1 is a perspective view schematically showing the architecture of a pattern defect inspecting device according to the present invention.

The following is a description, with references to the drawings, of the embodiments of the defect inspecting method and apparatus for inspecting patterns according to the present invention. FIG. 1 shows an example of a device according to the present invention. An X, Y, Z, θ (rotation) stage 2 is a stage on which is mounted a semiconductor wafer 1, an example of a pattern to be inspected. An objective lens 7 is used for image detection. It is referred to as an objective lens here, but it can also be referred to as an illumination lens since, in terms of the illumination, it applies the illuminating light to the specimen. An illuminating light source 3 (e.g., a UV laser with a wavelength of 266 nm) illuminates the semiconductor wafer 1, respectively the sample having the pattern to be inspected. A beam splitter 5 (in some cases a polarizing beam splitter) reflects the illuminating light from the illuminating light source 7 and provides bright-field illumination, for example, to the semiconductor wafer 1 through the objective lens 7. There is also shown a ¼ wave plate 6. A scanning mechanism 4 is used to scan the laser beam from the light source over the pupil of the objective lens 7. An image sensor 8 outputs a concentration image signal based on the brightness (concentration) of the reflected light from the semiconductor wafer 1. An A/D converter 9 converts the concentration image signal obtained from the image sensor 8 into a digital signal. A 10-bit converter can be used, for example.

The stage 2 is operated so that the semiconductor wafer 1 is moved at a uniform speed. The image sensor 8 detects the brightness information (concentration information) of the inspected pattern formed on the semiconductor wafer 1.

A tone converter 10 performs tone conversion, as described in Japanese laid-open patent publication number Hei 8-320294, on the 10-bit digital image signal output from the A/D converter 9. The tone converter 10 employs logarithmic conversion, exponential conversion, polynomial conversion, and the like to adjust the image. The tone converter 10 is formed to output, for example, 8-bit digital signals. A delay memory 11 stores and delays the image signal output from the tone converter 10. The delay corresponds to the interval for a single cell, multiple cells, a single chip, or multiple chips, i.e., repeating sections from the output image signal of the semiconductor wafer. A cell is a repeated unit of the chip pattern.

comparator 12 detects defects by comparing the tone-converted image signal from the tone converter 10 with the delayed image signal obtained from the delay memory 11.

The comparator 12 compares an image from the delay memory 11 with the detected image. The delayed image is delayed by an interval corresponding to the cell pitch or the like. Coordinates for data relating to the arrangement of the semiconductor wafer 1 and the like are entered using inputting means 15, such as a keyboard, disk, or the like. Based on the coordinates for data relating to the arrangement of the semiconductor wafer 1 and the like, a CPU 13 generates defect inspection data and stores it into a storage device 14. This defect inspection data can be displayed as needed on displaying means, such as a display unit, and can also be output to outputting means.

Specifically, the comparator can be the one described in Japanese laid-open patent publication number Sho 61-212708 or the like. The comparator can, for example, be formed from: an image alignment circuit; a differential image detection circuit for aligned images; a disparity detection circuit that binaries the differential image; and a characteristics extraction circuit that uses the binarized output to calculate areas, lengths (projected lengths), coordinates, and the like. One embodiment will be described in detail later.

Next, the light source 3 will be described. Shorter wavelengths are required for high resolutions, but with UV wavelengths, which are the most effective for this, high levels of illumination are difficult to obtain. Discharge lamps are very effective as UV light sources. In particular, mercury xenon lamps provide stronger emission lines in the UV range compared to other discharge lamps.

Figure 2:
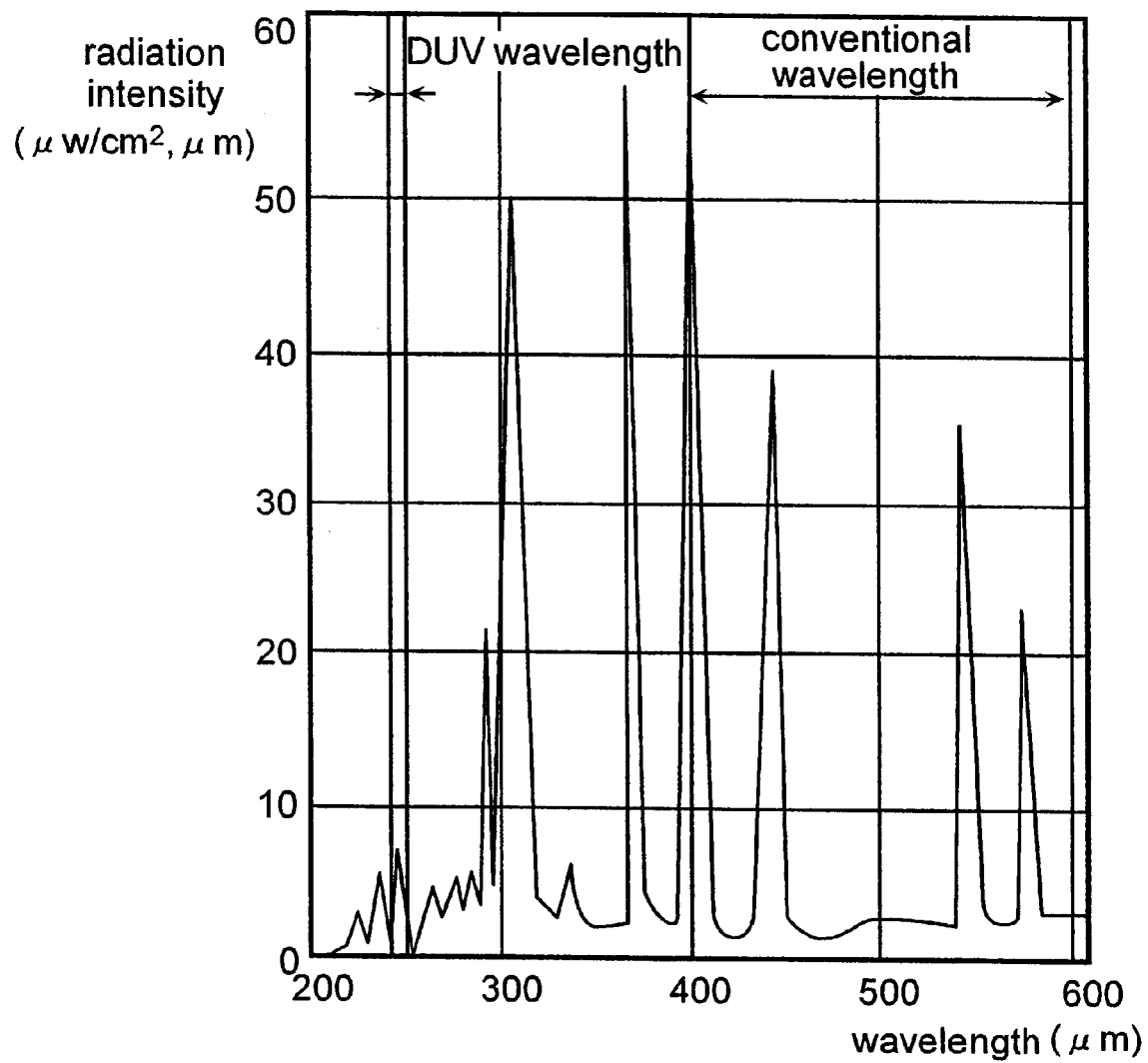
FIG. 2 is a graph illustrating an emission spectrum of discharge tube illumination.

FIG. 2 shows an example of the relation between radiation intensity and wavelength in a mercury xenon lamp. Compared to the wide wavelength range of conventional visible light, the emission lines in the DUV range are only 1–2% of the total output light (about 30% for the visible range). Also, the light is lacking in directionality, and the effectiveness with which the light from the discharge lamp reaches the specimen is not very high, even with a carefully designed optical system. Thus, something must be done to allow a discharge lamp to provide enough light in the UV range for high-speed image detection.

Using a high-output discharge lamp to improve the illumination (luminance) on the specimen only results in a larger illuminating spot compared to a low-output lamp. Thus, the luminance (optical power per unit area) does not actually improve. Thus, a laser would be suited as a light source providing effective, high-luminance illumination in the UV range.

Using a laser as a light source provides significant advantages. In the embodiments of the present invention described below, the descriptions will focus on cases where a laser is used as a light source.

However, this concept of the present invention is not restricted to these embodiments. Clearly, a discharge lamp, especially a mercury xenon lamp, can be used as a light source while still providing similar advantages as the pattern defect inspection method and apparatus described below that uses a laser as the light source.

Figure 3:
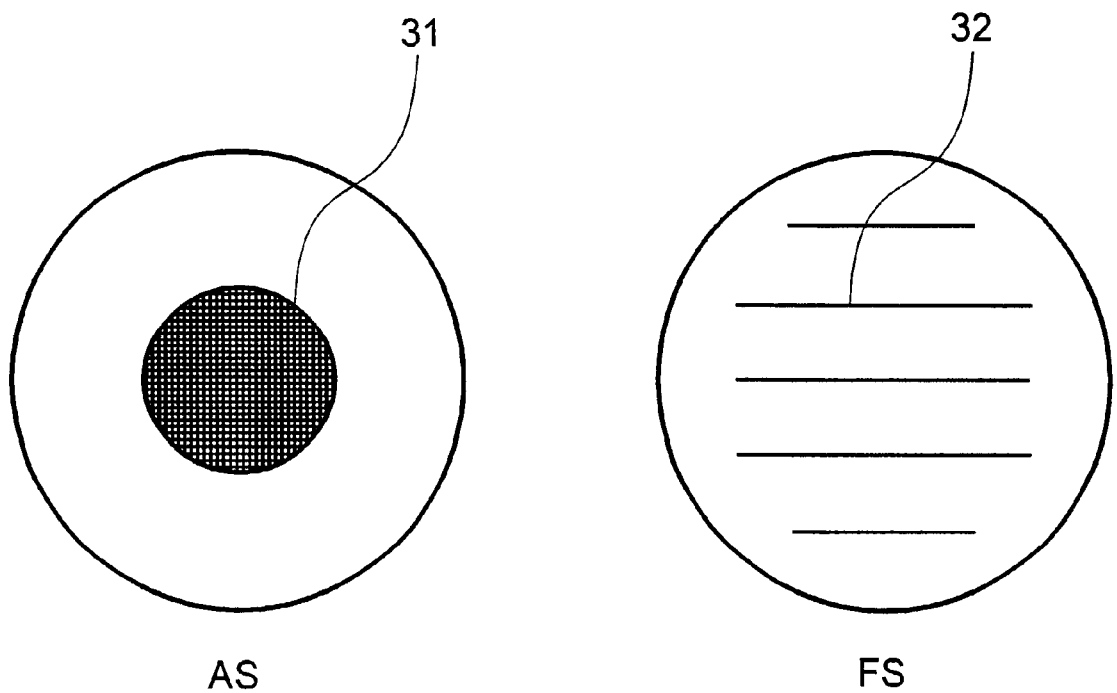
FIGS. 3($a$) and 3($b$) are diagrams showing the illumination from discharge tube illumination on a pupil of a detection/objective lens and on the field of view, respectively.

FIGS. 3(a) and 3(b) show illumination under standard white light of the objective lens pupil and the field of view, respectively, wherein AS indicates the pupil and FS indicates the field of view. An image 31 from the light source is formed at the pupil position, and a roughly uniform illumination 32 is applied to the entire field of view.

Figure 4:
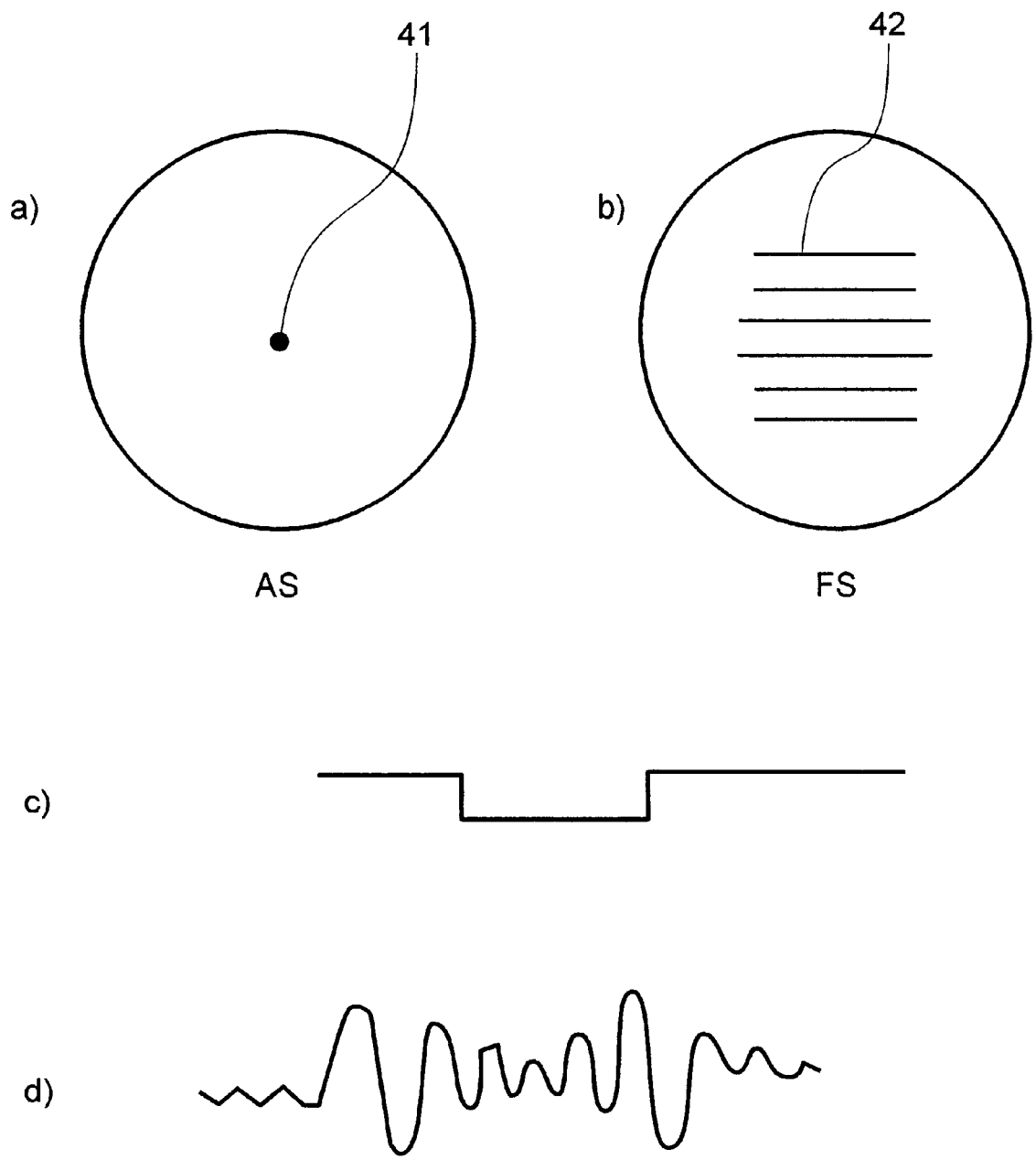
FIG. 4($a$) is a diagram showing the illumination from laser illumination on a pupil of a detection/objective lens.

Next, the use of a laser light source is illustrated in FIGS. 4(a) to 4(d). In this case, as seen in FIG. 4(a), a light-source image 41 at the pupil position is formed as a point. On the field of view, as seen in FIG. 4(b), an illumination 42 is applied to the circuit pattern. If the circuit pattern has a cross-section as shown in FIG. 4(c), an image based on the detected waveform shown in FIG. 4(d) is obtained. When illuminating a circuit pattern with a laser beam and obtaining an image of the circuit pattern in this manner, the σ of the illumination, which can cause overshooting, undershooting, and speckling, is small. Another way of stating this is that illumination is not applied from various angles to the viewing field under the objective lens. With normal white-light illumination, illumination of a certain size is applied to the pupil, and this illumination is directed with a range of angles corresponding to the NA (numerical aperture) of the objective lens with relation to the viewing field.

Figure 5:
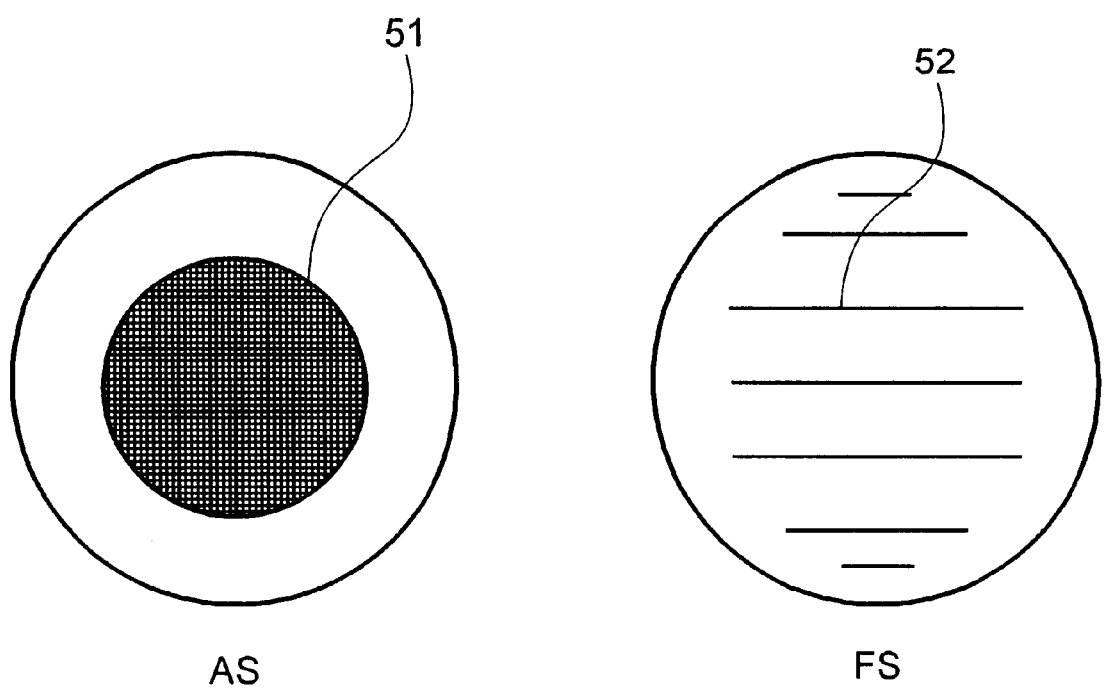
FIGS. 5($a$) and 5($b$) are diagrams showing the illumination from laser illumination, with the pupil expanded, on the pupil of a detection/objective lens and on the field of view, respectively.

With coherent light, such as from a laser, the σ (which is proportional to the size of the light source on the pupil) is 0. This is because the light-source image from coherent light is a point, resulting in a point image on the pupil. Of course, a different lens system can be used to project a wider light-beam 51 to the pupil, as shown in FIGS. 5(a) and 5(b). However, the coherence of the laser will provide results 52 which are identical to that when all light is emanating from a position where σ=0, which does not solve the problem. Thus, a way to reduce the coherence of the laser light is necessary. Reducing the coherence involves reducing either the coherence time or the coherence space.

In accordance with the present invention, a light-source image is formed on the pupil of the objective lens of the detection device. An illumination 65 is applied to the field of view by scanning. For example, a position 61 in FIG. 6(a) is illuminated first, then a position 62, then a position 63, and the like. When doing this, images at these positions will contain speckling, overshooting, and undershooting, but there will be no interference from each position since the images are obtained at different times. Thus, when the images are added by the detector, the resulting image will be the same as one that would be obtained from an incoherent light source. To allow the detector to add up the images, a storage-type detector such as a CCD, would be suitable.

Figure 19:
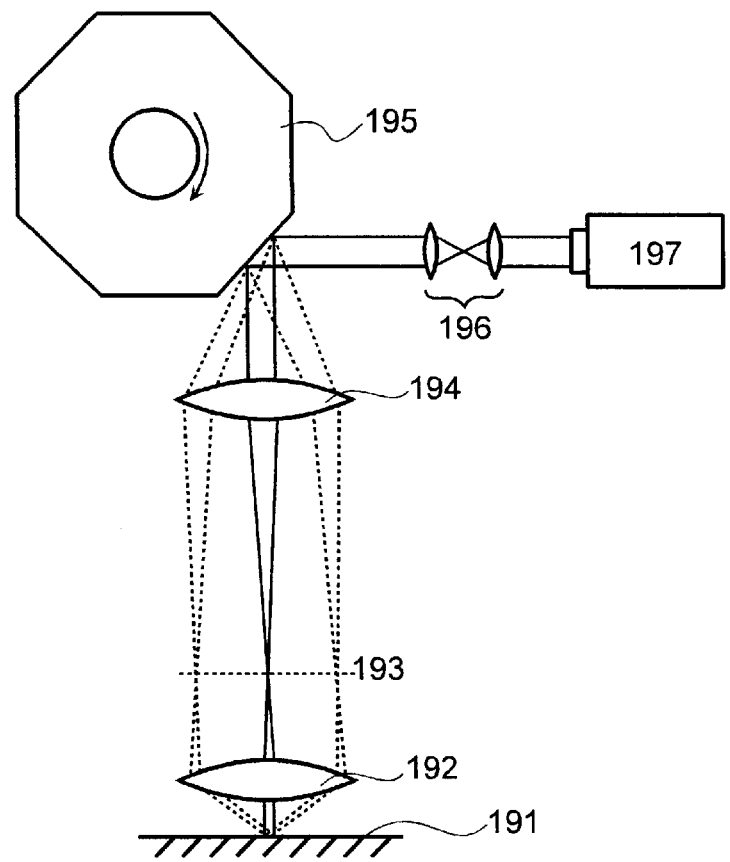
FIG. 19 is a schematic diagram of a laser illumination optical system according to the present invention.

FIG. 19 shows an arrangement for using a laser spot to scan the pupil of the object (detection/illumination) lens. This figure shows the architecture for illumination, and the detection architecture is omitted. Also, the scanning mechanism is shown for one dimension only in order to indicate the principles.

A laser light source 197 projects a beam (which is collimated, since it is a laser beam). A beam shaping mechanism 196 shapes the beam to the needed shape. The beam is then deflected by a scanning mechanism 195. In this example, a polygon mirror is used as the scanning mechanism. The deflection angle of the scanned collimated beam is changed to a displacement by an f-θ lens 194, known as a condensing lens. The lens 194 is separated from the scanning mirror surface by the focal distance of the lens 194. The lens 194 focuses light onto a pupil surface 193 of the objective lens 192. Thus, the distance between the lens 194 and the pupil surface 193 is also the focal distance of the lens 194. With this arrangement, the laser beam from the objective lens 192 is illuminated onto a specimen 191 as a collimated beam with a changing angle.

Figure 20:
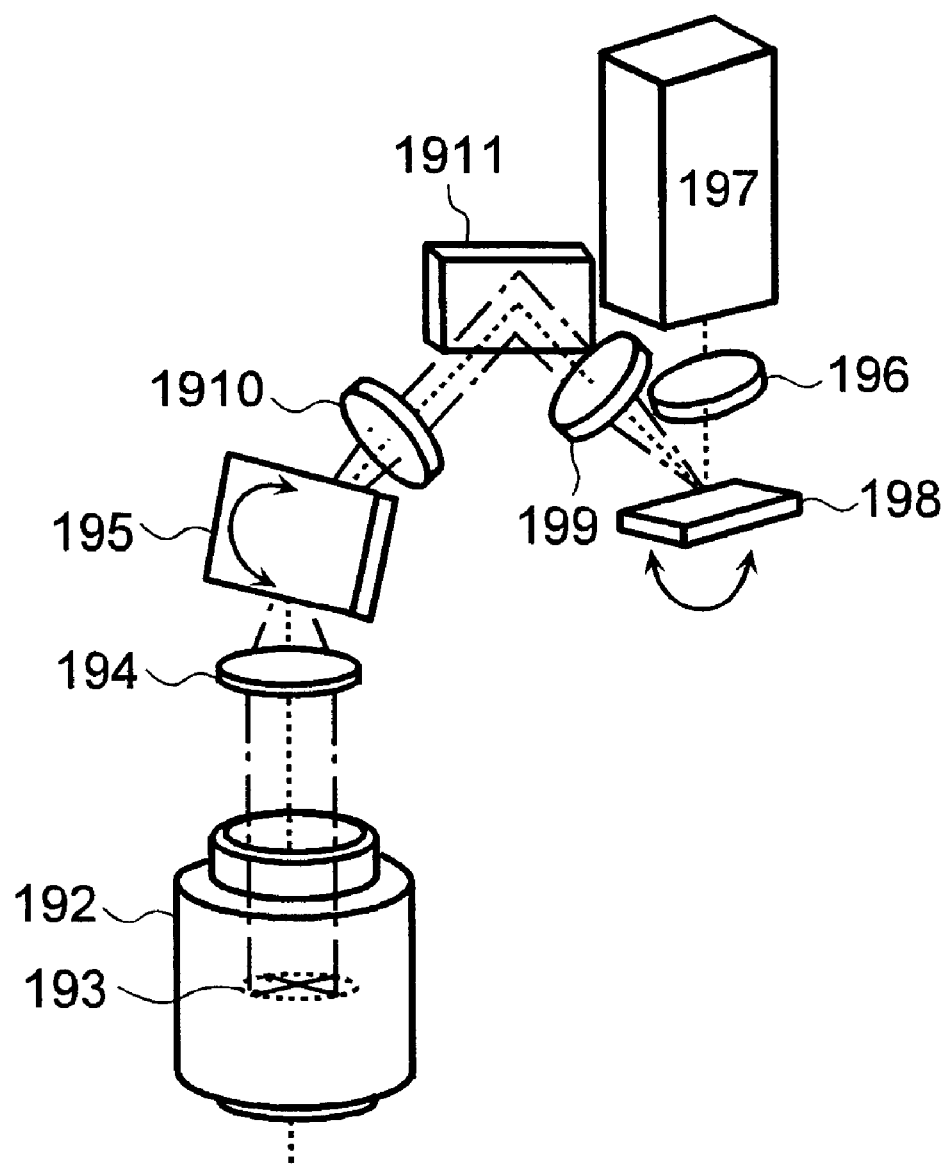
FIG. 20 is a perspective view schematically showing a laser illumination optical system according to the present invention.

FIG. 20 shows an example where a laser beam scans the pupil two-dimensionally. In this figure, a plate-type mirror, such as a galvano-mirror, is shown as a sample scanning mechanism. A mirror 1911 in the figure is used to bend the optical path, but is not required. The differences from the structure shown in FIG. 19 are the additions of a f-θ lens 199, a scanning mirror 198 serving as the scanning mechanism for another axis, and an incident lens 1910 for the scanning mirror 195.

In the figure, two-dimensional scanning as indicated in FIG. 6(a) is performed.

Figure 21:
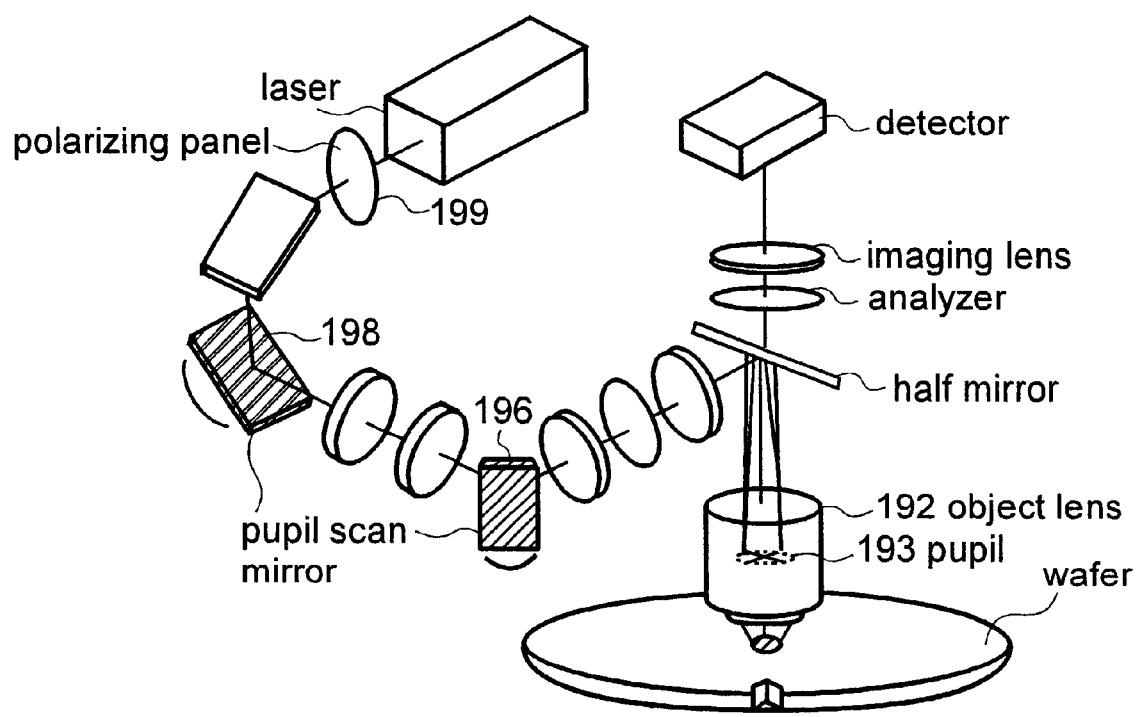
FIG. 21 is a perspective view schematically showing a laser illumination optical system according to the present invention.

The NA of the objective lens 192 in this embodiment is 0.75. With a larger NA, pupil scanning is more effective and there is a reduction in the influence of thin film interference in the specimen pattern. (Differing brightnesses result from patterns with differing thicknesses, increasing the differences in normal sections in the pattern comparison described later. This makes detection of fine defects difficult. There are significant changes in brightness even in the very small thickness variations known as grains and hillocks.) FIG. 21 shows an example where a diffuser panel is placed in the optical path. The diffuser panel is disposed at a position that is conjugate to both the objective lens 192 and the pupil 193. In this example, the laser beam scans the diffuser plate so that there is a greater reduction of coherency. Of course, the diffuser plate can be rotated or moved at high speeds in a reciprocating manner in a direction perpendicular to the optical axis of the laser beam.

Figure 17:
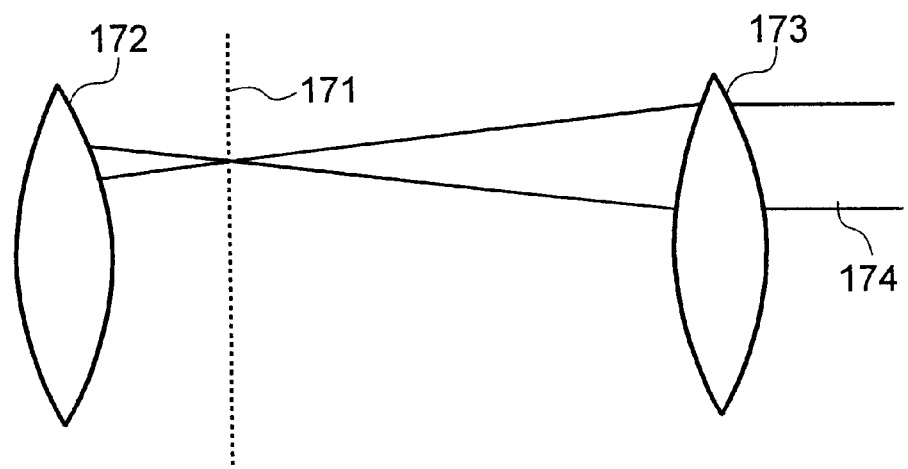
FIG. 17 is a diagram of an optical system according to the present invention.

As shown in FIG. 17, in the formation of the light-source image on the pupil, the focus lens focuses the light from the laser light source onto the pupil surface 171 of the objective lens 172 (in detection involving top lighting, the illumination lens also serves as the detection lens). Here, the laser light source is a point light source, so that a spotlight is applied to a point that has been reduced as much as possible while still allowing analysis. In other words, the entire output of the laser is focused on this spot, resulting in considerable power at this point.

The objective lens is actually formed as a lens group from a large number (ten or more in some cases) to compensate for aberration. The design of the objective lens may result in some cases in the pupil being positioned inside a lens (in the glass) or in the vicinity of a lens surface rather than away from the lenses. In such cases, the coating applied to the lenses (antireflection coating and the like) can be damaged by the high-power laser beam. This can happen because, while standard laser confocal microscopes known as laser scanning microscopes use a laser beam that expands on the pupil surface, the present invention forms a spot on the pupil surface (with laser scanning microscopes, however, a spot is focused on the specimen, which can lead to damage to the specimen).

The power of a spot is higher for smaller spots even if the total power is the same. The average power density is defined using the total power and the spot area, determined from the spot diameter, as follows.

Average power density=total power/spot area

Figure 18:
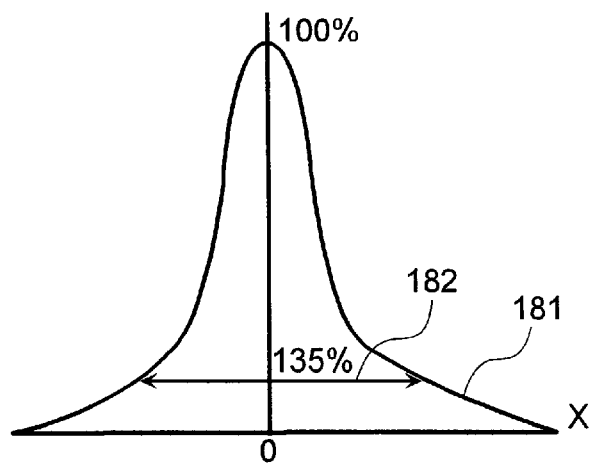
FIG. 18 is a diagram illustrating the intensity distribution of a beam from a laser light source.

FIG. 18 shows across-section of an intensity distribution 181 of a laser beam. The laser beam exhibits a typical laser beam shape with a distribution known as a Gaussian distribution that goes up at the center and tapers down on either side. Defining a spot diameter for a gently descending distribution is difficult, but a level 182, where the intensity is 13.5% of the peak intensity, is used here. Based on this definition, the power density at the peak in a Gaussian distribution is twice the overall average power density.

Based on tests performed by the inventors, the average power density at which a coating is damaged is 200 W/mm2 (with a peak power density of 400 W/mm2). As long as this value is not exceeded, there is no damage to the coating. In accordance with the present invention, the pupil in the objective lens plays a large role, and the problem of coating damage can be avoided by designing the lens so that the pupil position is kept away from the glass lens surfaces. This unfocuses the spot so that the diameter is somewhat increased and the average power density is reduced. Based on tests and studies performed by the inventors, a distance of at least 5 mm, approximately, is required.

If the configuration of the objective lens prevents adequate distance from being provided, it would also be possible to leave just that particular lens uncoated. Simply leaving some of the lenses uncoated will not have a significant effect on the transmittance of the objective lens as a whole, and the inventors believe that this can also deal with issues of coating endurance.

Also, it would be desirable to use a continuous-wave laser as the laser light source. While a pulse laser can keep the average output down, the peak value of the pulses result in the application of very high power, which can lead to damage. Of course, pulse lasers can be used if the lasers have a low output that will not lead to damage.

Figure 26:
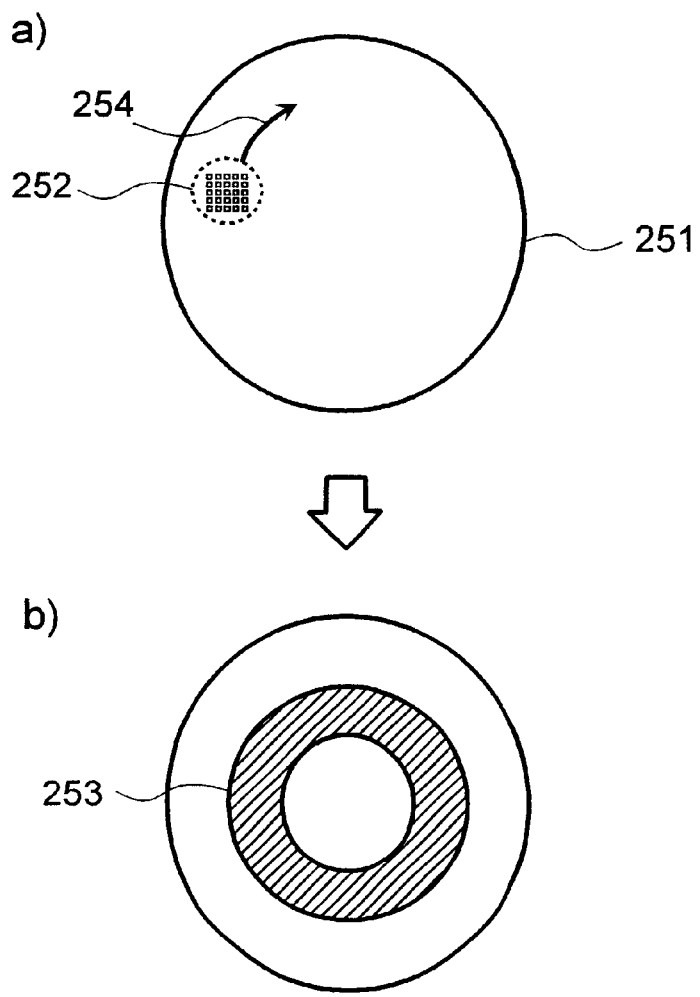
FIG. 26 is a diagram illustrating how ring-shaped illumination is performed using laser illumination according to the present invention.

With the pupil spot scanning, as described above, the scanning can be performed as a spiral scan 66 or a video-type (raster) scan 67, as shown in FIG. 6(c) and FIG. 6(d). Other scanning methods can be used as well. However, it would be desirable to have a single scanning unit within the storage interval of the detector. Thus, scanning should be done in synchronization with the operations of the detector. For example, in the architecture shown in FIG. 20 or FIG. 21, where the pupil is scanned in a ring-shaped manner (as shown in FIG. 26 to be described later), if the storage time of the image sensor is 1 ms, galvano-mirrors 195, 198 should be driven to operate with a primitive period of 1 kHz. Furthermore, it would be desirable for the stage, the sensor, and the pupil scanning to be operated in synchronization. In this case, the stage will have the greatest inertia, making it the most difficult to operate in synchronization. In pupil scanning optical systems, synchronizat ion may be easier with broader frequency ranges or limited frequency ranges, depending on the type of device. Since the sensor is an electronic circuit, synchronization is easy. Thus, it would be easy and desirable to generate a synchronization signal based on the stage position, and to then have the other two elements synchronized to this.

Figure 16:
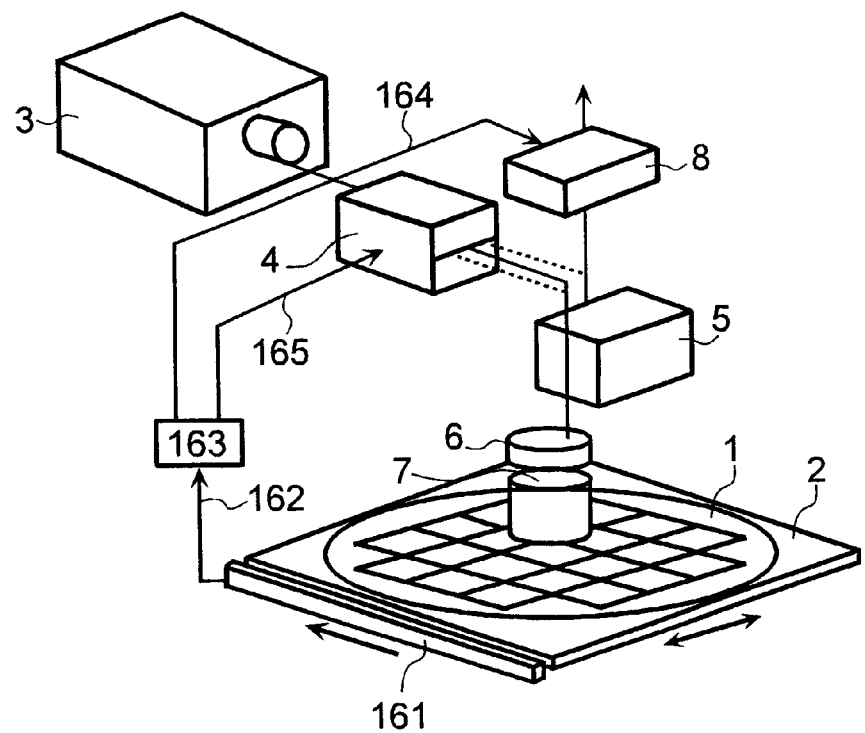
FIG. 16 is a perspective view schematically showing a schematic architecture of a pattern defect inspecting device according to the present invention.

FIG. 16 shows this kind of system. The stage position is determined by a position detecting mechanism 161, such as a linear encoder attached to the XY stage 2. A synchronization signal generator 163 generates a synchronization signal 164, such as a sensor transfer pulse, and a synchronization signal 165 for the pupil scanning mechanism.

With a pupil scanning mechanism, synchronization is easiest when an electronic signal is converted directly into a light deflection angle, as in A/0 deflectors, E/O deflectors, and the like. Also, deflectors based on mirrors, such as galvano-mirrors and polygon mirrors, can be used.

With this arrangement, an image of the illumination 65 for the entire field of view can be obtained, as shown in FIG. 6(b).

Figure 7:
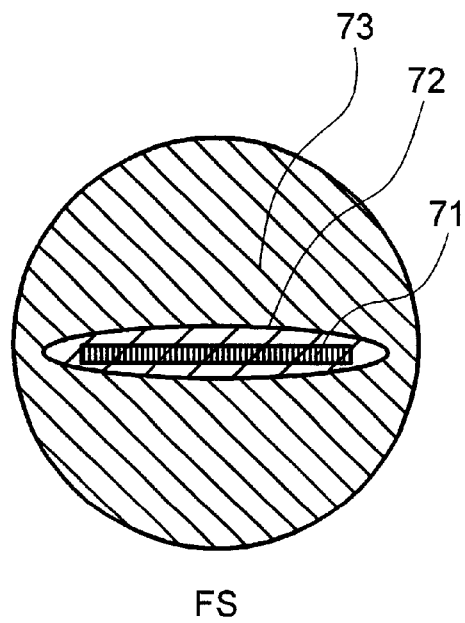
FIG. 7 is a diagram showing the relationship between a CCD detector and an illumination area on the field of view according to the present invention.
Figure 8:
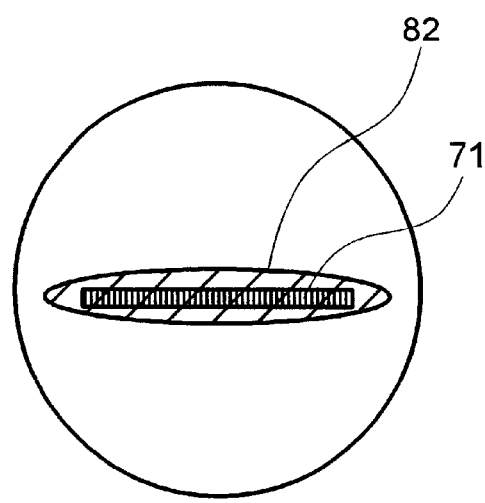
FIG. 8 is a diagram showing the relationship between a CCD detector and an illumination area on the field of view according to the present invention.
Figure 9:
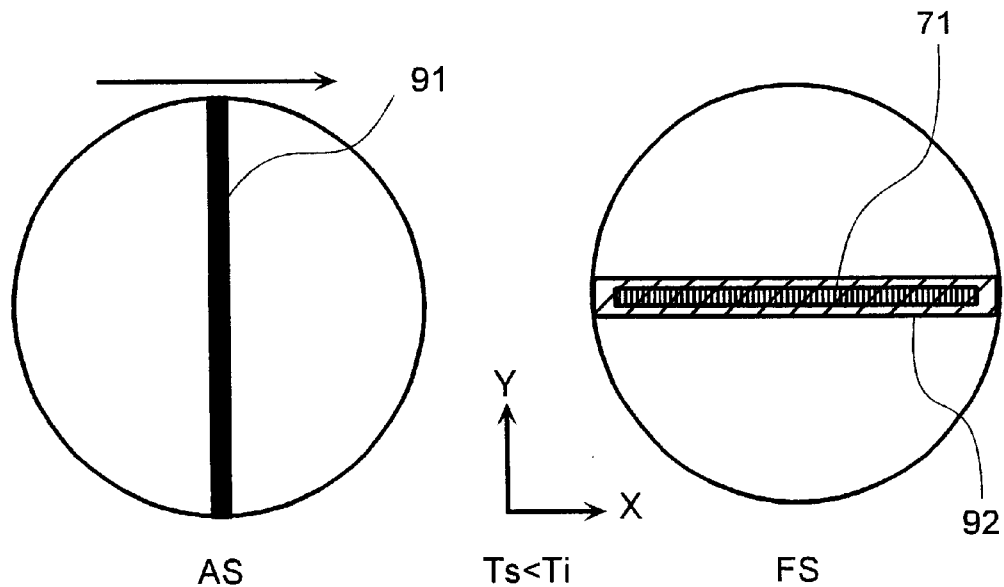
FIGS. 9($a$) and 9($b$) are diagrams showing the relationship between a CCD detector and the illumination on the field of view from laser illumination according to the present invention.

Next, the use of a one-dimensional sensor with a storage-type detector will be considered. As shown in FIG. 7, even if the entire field of view of a one-dimensional sensor 71 is illuminated, only the illumination at a region 72 will contribute to detection, while a region 73, which takes up the majority of the optical power, will not contribute thereto. To improve the illumination, it would be desirable to provide linear illumination on the one-dimensional sensor 71, as shown in a region 82 in FIG. 8. (A two-dimensional image can be obtained by scanning the CCD along the Y axis of the field of view.) In this case, as indicated in a region 91 in FIG. 9(a), illumination can be applied on the pupil longitudinally along the Y axis in the figure so that an illumination 92 suited to the shape of the CCD 71 can be provided for the field of view, as seen in FIG. 9(b). Also, scanning along the X axis is performed over the pupil. A period Ts used for the scanning is set to be shorter than a storage time Ti of the CCD. This allows the image to be accumulated.

Figure 10:
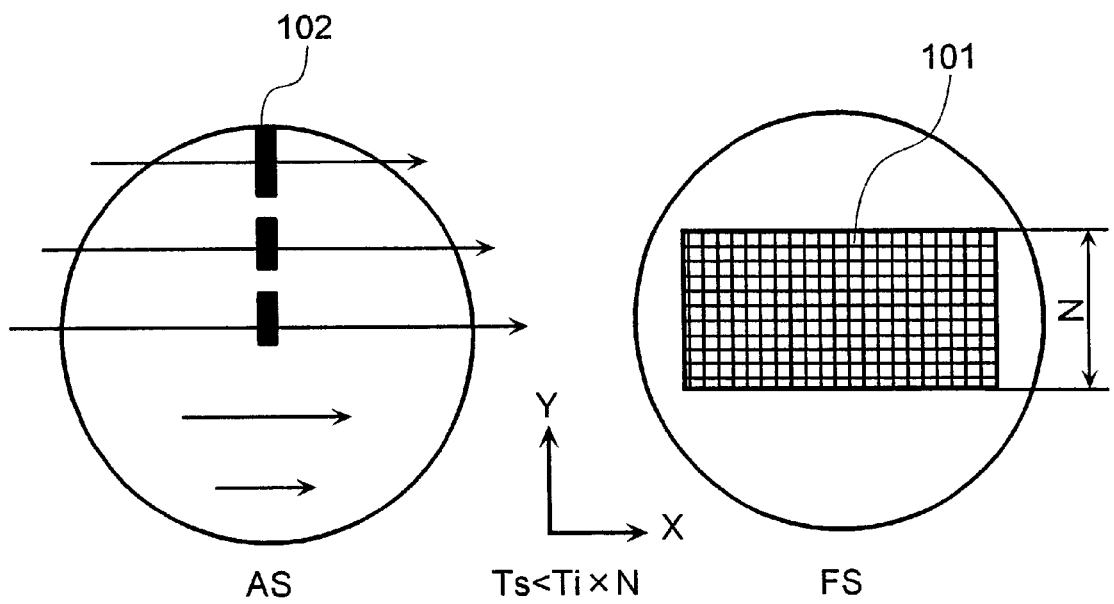
FIGS. 10($a$) and 10($b$) are diagrams showing the relationship between a TDI detector and the illumination on the field of view from laser illumination according to the present invention.

The problem with this type of scanning is that scanning is already extended along the Y axis over the pupil, preventing scanning along the Y axis. Thus, the overshooting and undershooting that take place along the Y axis of the CCD in the field of view cannot be reduced. Conversely, if the length along the Y axis is reduced to allow scanning along the Y axis over the pupil, the width along the Y axis over the field of view is increased, thus reducing the illumination. According to the present invention this problem is solved by using a TDI (Time Delay and Integration) CCD sensor, as shown in FIG. 10(a). With a TDI sensor, N stages (where N is approximately a few dozen to 256 stages) of light-receiving sections known as stages are arranged. Thus, even if the width of the illuminated area on the field of view increases by a factor of N, the illumination will still be used effectively for detection.

Thus, with this CCD the Y-axis length of a focus 102 over the pupil can be reduced to approximately 1/N, and scanning can be performed in both the X and Y directions over the-pupil. This allows overshooting and undershooting generated by the TDI in both the X and Y directions of the field of view to be reduced, resulting in a good detection images. Also, taking the illumination distribution generated on the field of view into consideration, it would be desirable in terms of uniform detection for Ts to be shorter than ½ the product of N and Ti. It would also be desirable in terms of uniform defection for focusing to take place through a fly-eye or integrator lens rather than focusing the light from the laser light source directly on the pupil.

Figure 11:
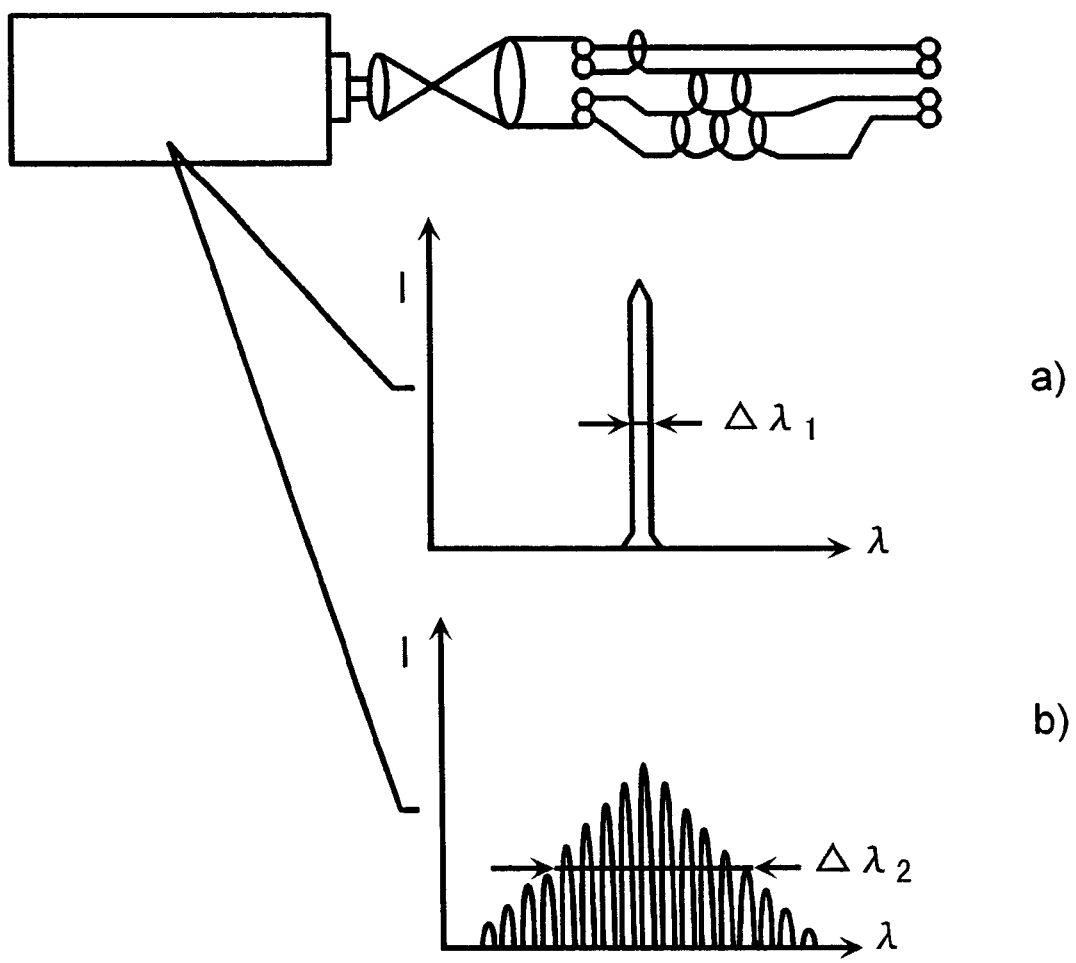
FIG. 11 is a schematic diagram of the architecture for reducing spatial coherence of laser illumination according to the present invention.

Next, a way to reduce spatial coherence will be described. Spatial coherence can be provided by using a light that has an optical-path difference longer than the coherence length of the laser. More specifically, the output from a laser can be passed through bundled optical fibers 111 having different lengths, as shown in FIG. 11. The output light from this would be incoherent light. If these are arranged over the pupil, an image can be obtained without overshooting, undershooting, and speckling. With this system, it would be better to have a shorter coherence length for the laser light source. Rather than a single vertical mode (emission spectrum) with a narrow band $\Delta\lambda 1$ as shown in FIG. 11($a$), it would be desirable for this person to have an emission with multiple vertical modes and a wider band of $\Delta\lambda 2$ as shown in FIG. 11($b$).

Figure 12:
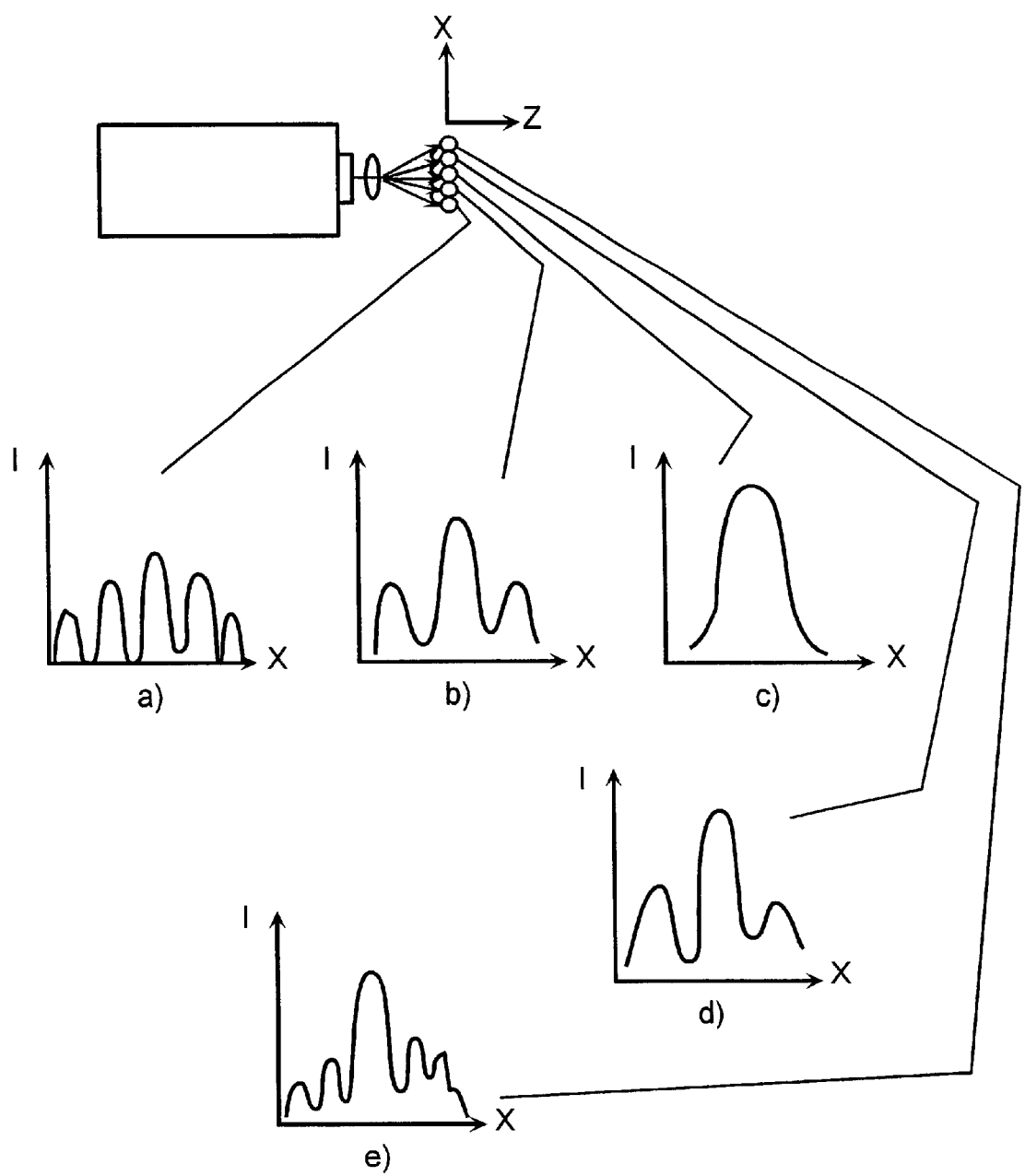
FIG. 12 is a schematic diagram of the architecture for reducing spatial coherence of laser illumination according to the present invention.

Another way of reducing spatial coherence is to take advantage of the phenomenon where, when light is projected into an optical fiber with an offset in the optical axis, the lateral mode (spatial distribution, the optical intensity 1 with relation to space) of the exit beam changes. This type of mode change is generally considered an undesirable phenomenon in industrial applications, and reduction of the lateral mode change is usually attempted. However, this method takes advantage of this. As shown in FIG. 12, the various offsets are intentionally applied to the optical axes when projecting light into the fibers 121. This results in exit beams (a), (b), (c), (d), and (e), with various lateral mode changes. This causes the resulting exit lights to be incoherent with relation to each other, and these are arranged over the pupil. With this method, an extremely large number of light sources (bright spots on the pupil) can be obtained by bundling multiple fibers.

Figure 13:
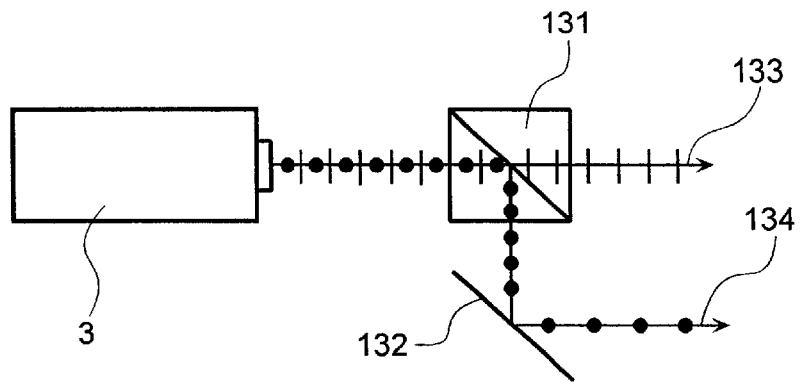
FIG. 13 is a schematic diagram of the architecture for reducing spatial coherence of laser illumination according to the present invention.

FIG. 13 shows how a polarized beam splitter 131 is used to split the exit beam from the laser light source 3 into two beams 133, 134 having perpendicular polarization planes. A mirror 132 changes the direction of the beam. Since beams with perpendicular polarization planes do not have coherence, light with no coherence can be obtained using a very simple structure. This method can only provide two beams, but by combining this with the method described above, light with no coherence can be obtained with half the effort.

Figure 14:
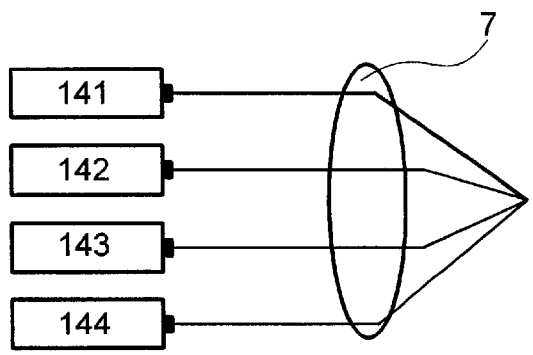
FIG. 14 is a schematic diagram of the architecture for reducing spatial coherence of laser illumination according to the present invention.
Figure 15:
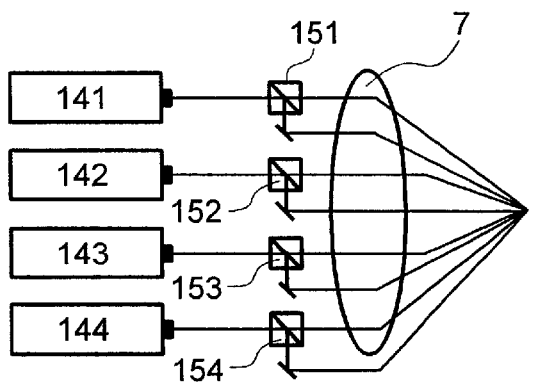
FIG. 15 is a schematic diagram of the architecture for reducing spatial coherence of laser illumination according to the present invention.

Also, since independent light sources do not have coherence, independent light sources 141, 142, 143, 144, ... can be used so that they illuminate points on the pupil of the objective lens 7, as shown in FIG. 14. Also, as described above, polarizing beam splitters 151–154 can be combined, as shown in FIG. 15. This can reduce the number of laser light sources by half and keep costs low.

The description above presented a number of ways to reduce the coherence of, a laser beam and illuminate multiple points on the pupil so that the light can be focused on the objective lens to provide an image. These methods can also be combined or other equivalent reduction methods can be used as well.

Furthermore, if, as in the present invention, laser illumination is performed using a vibrating (or spinning) mirror or the like in the optical path to partially change the illumination optical path, with images of the illumination from the optical paths being accumulated over time to detect an image, temporal coherence is reduced in the process so spatial coherence does not need to be reduced as strictly as described above.

Figure 22:
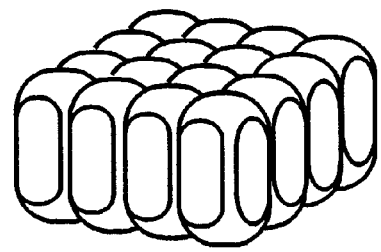
FIG. 22 is a perspective view of a set of glass rod lenses according to the present invention.
Figure 23:
FIG. 23 is a perspective view of a multi-cylindrical lens array according to the present invention.

More specifically, when forming multiple bright spots on the pupil surface as described above, the optical path difference does not have to be at or less than the coherence length. For example, a set of glass rod lenses having uniform lengths (a fly-eye lens) can be used to generate multiple light sources from a single laser light source, as shown in FIG. 22. Also, as shown in FIG. 23, a multi-cylindrical lens array, which has a simpler structure than the set of glass rod lenses, can be used. With a multi-cylindrical lens array, multiple light sources can be generated in one direction only. By arranging two arrays in a perpendicular manner, multiple light sources can be generated in two dimensions. Also, if this is done, the pitch between the arrays can be changed so that light sources having different vertical and horizontal light source pitches can be generated.

Another advantage of this system is that it would be possible, as shown in FIG. 26 for example, to form a light source group on a pupil surface 251 with a different magnification. Then, the light source group 252 can, for example, be rotationally scanned in a ring, as indicated by an arrow 254. As a result, a pupil surface distribution 253 indicated by the shading n FIG. 26 is formed, thus providing a ring-shaped illumination that allows improved resolution in the detected image. Also, the ring-shaped illumination conditions can be changed just by changing the magnification of the light source group. Further advantages are provided when using a TDI image sensor with N stages and a scan rate of 1 kHz. The entire surface of the pupil can be scanned with a galvano-mirror having a primitive period of 1 kHz/N. Galvano-mirrors with multi-kHz periods are commercially available, and combining this with a TDI image sensor provides pupil scanning at a practical speed and high-speed image detection. The number of stages in the TDI image sensor should match the speed of the galvano-mirror. Also, if a TDI image sensor with a variable number of stages is used, the storage time can be changed based on the pupil scanning method.

Figure 24:
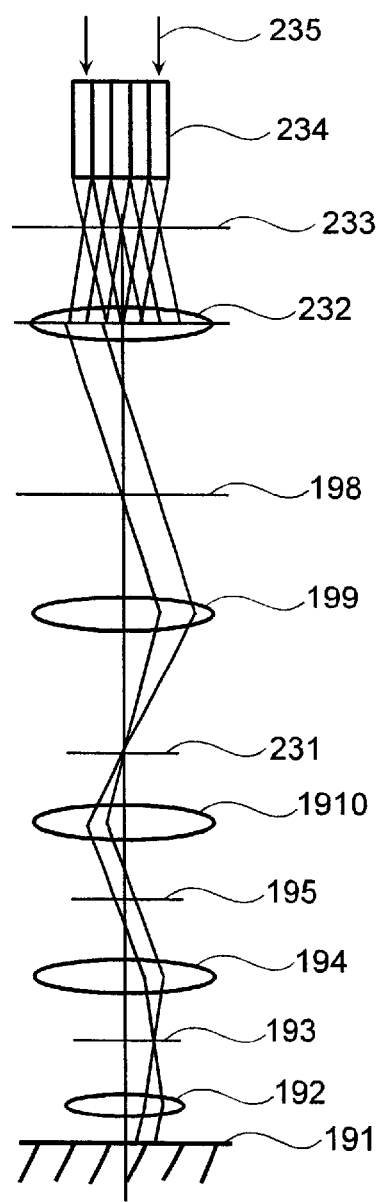
FIG. 24 is a schematic diagram of the architecture of a mechanism for scanning a pupil with laser illumination according to the present invention.

FIG. 24 is a schematic diagram of an illumination system using the lens array described above. A correct representation would provide three dimensions as in FIG. 20, but this would not allow the focusing of light, which is important here, to be meaningfully illustrated, so a schematic representation is used instead. A collimated beam 235 from a laser is projected at a lens array 234 to generate multiple bright spots (new light sources) on a second pupil conjugate surface 233 conjugate to the pupil surface 193 of the objective lens 192. From here, multiple beams are projected, but this description will concentrate on one beam, which is indicated in FIG. 24. The light from this new set of light sources is converted to a roughly collimated beam by a second projection lens 232 and is then projected onto a second scanning mirror surface 198.

The light reflected here is passed through a second focusing lens 199 to a first pupil conjugate surface 231. A first projection lens 1910 then converts it to roughly collimated light, which is projected to the other first scanning mirror surface 195. A first focusing lens focuses the light onto the pupil surface 193, and the objective lens 192 converts it to roughly collimated light, which then illuminates the specimen surface 191. The advantage of this system is that the outputs of the multiple bright spots that are generated correspond to the intensity distribution of the original Gaussian beam 235 so that when these overlap on the specimen 191 the resulting illumination has minimal illumination distribution.

In addition to providing higher resolutions through shorter wavelengths, methods for enhancing contrasts in patterns will be described.

Figure 25:
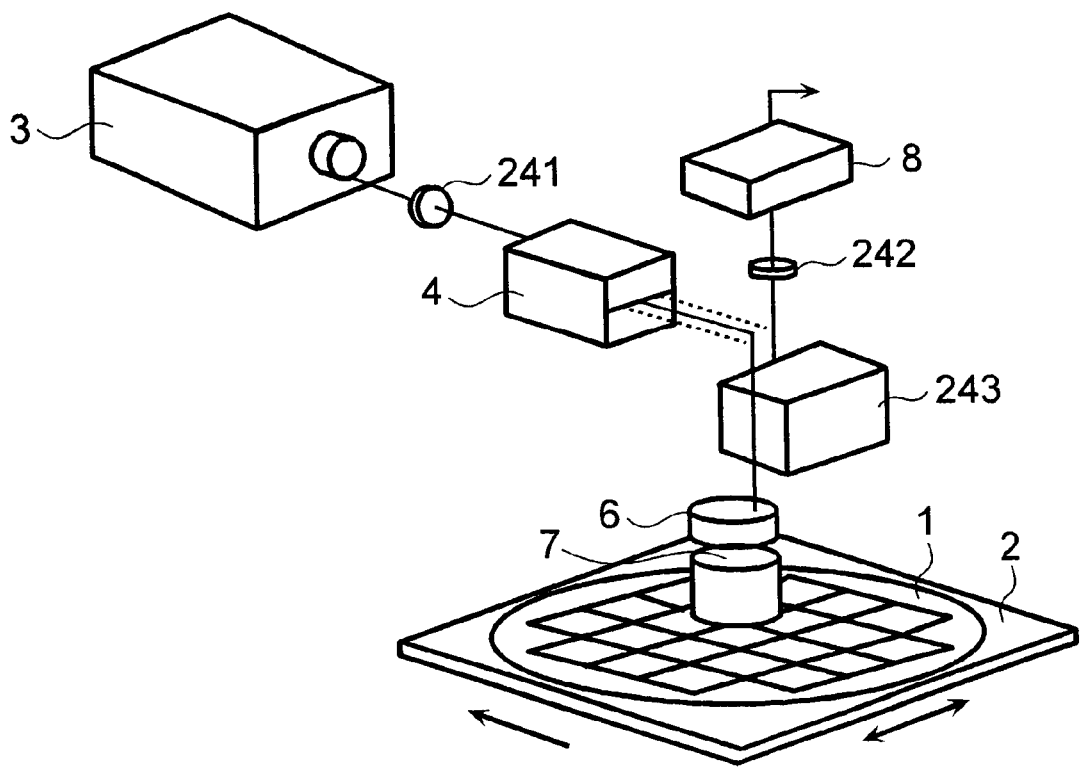
FIG. 25 is a perspective view schematically showing a mechanism for controlling polarization of laser illumination according to the present invention.

The ability to freely control the polarization of the laser was considered in attempting to enhance pattern contrast. By controlling the direction of polarization and the ellipticity of the illuminating light, a partial polarized component of the detection light could be detected. In FIG. 25, an improvement is made to the optical system from FIG. 1.

Laser illumination is characterized in having a single wavelength and having linear polarization. Thus, polarization can be controlled with a high degree of effectiveness by placing a polarizing element 241, e.g., a half-wave plate and a quarter-wave plate, in the optical path. The polarization can be controlled, for example, by rotating the half-wave plate and the quarter wave-plate or the like around the optical axis. The polarization of the illumination can greatly change the pattern contrast. Thus, the performance of the optical system can be improved by allowing the polarization to be controlled (rotating and positioning wave plates). More specifically, linear polarization orientation can be controlled with the half-wave plate and ellipticity can be changed with the quarter-wave plate.

Also, an analyzer 242 disposed on the detection side of the structure can extract desired polarization components. This allows components that do not contribute to defect detection, e.g., zero-order light, to be reduced while optical components, such as diffracted light, that contribute to defect detection, including pattern edges, can be increased. This improves the detection sensitivity. The analyzer can be rotated according to the polarization.

With this combination, both cross-polarization and parallel polarization can be provided. Of course, circular polarization can also be provided. These are not dependent on the wavelength of the illumination. It would also be possible to use any other structure as long as these overall characteristics are established.

When the diffracted light from a pattern is observed at the pupil surface of the objective lens (although not indicated in FIG. 25, a system for observing the pupil can be provided easily), it can be confirmed that the zero-order light can be attenuated compared to higher orders of diffracted light by selecting the polarization. As a result, low-frequency components can be attenuated and pattern contrast can be enhanced. Of course, zero-order light can also be attenuated by having a spatial filter disposed at a conjugate position relative to the objective lens and the pupil (depending on the spatial filter, diffracted light from the pattern may be blocked and diffuse light from contaminants can be guided to the image sensor).

However, controlling polarization can allow more efficient extraction of higher-order diffracted light.

According to tests performed by the inventors, contrast enhancements of approximately 20–300% were found. Also, the polarizing element 241 does not have to be disposed at the position shown in FIG. 25 and can instead be positioned where the desired properties can be obtained (e.g., between the half prism 241 and the quarter-wave plate 6).

Figure 27:
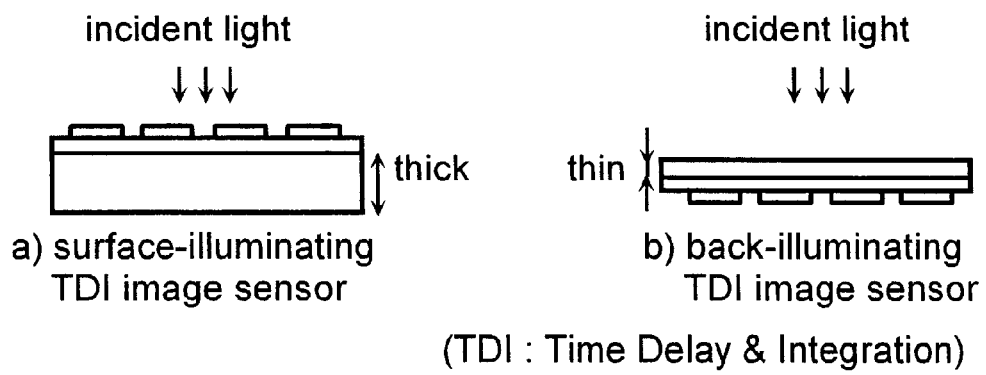
FIGS. 27(a) and 27(b) are side views of a TDI image sensor according to the present invention.

FIG. 27 shows the structure of the image sensor 8 used in FIG. 1. When a DUV laser light source is to be used, an image sensor that is sensitive to DUV must be used. Since the incident light passes through a gate to enter the CCD in surface-illuminating image sensors, short wavelengths in the incident light are attenuated, and there is almost no sensitivity to wavelengths at or below 400 nm. Thus, DUV light cannot be effectively detected. One way to obtain DUV sensitivity in surface-illuminating image sensors is to form the gate thin to reduce attenuation of shorter wavelengths.

Another method is to apply an organic thin-film coating to the cover glass so that visible light is emanated in response to application of DUV light. This allows DUV light to be detected by an image sensor that is only sensitive to visible light. Also, since back-illuminating image sensors apply light to the backside, where there are no gate structures, the quantum efficiency is high (e.g., 30% or higher), a large dynamic range is provided (e.g., 3000 or higher), and there is sensitivity to wavelengths of 400 nm or less, thus making it especially useful for illuminations at short wavelengths, e.g., under 200 nm. With this type of image sensor, a single image sensor can handle different illumination wavelengths.

By using a TDI (Time Delay Integrat ion) image sensor, high sensitivity can be provided. Furthermore, anti-blooming characteristics can be provided so that if there is more detected light than needed, the electric load will not saturate to the surrounding image elements.

Figure 28:
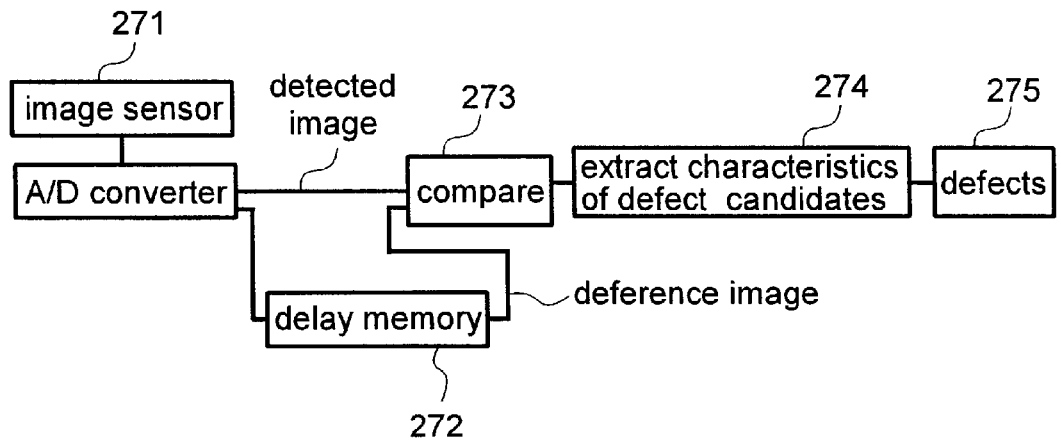
FIG. 28 is a schematic block diagram showing signal flows used to detect defects according to the present invention.

Next, an example of a processing system for detecting defects using an image received from the image sensor described above will be described with reference to FIG. 28. The inspected object has repeating patterns, so inspection involves extracting defect candidates through comparisons with adjacent patterns. The output signal from an image sensor 271 is converted into a digital signal through A/D conversion. To generate reference images to be used for comparisons, a delay memory 272 provides a delay corresponding to one pitch. As a result, the output from the delay memory is an image that is offset from the inspection image by one pitch.

A comparator 273 determines differences between corresponding image element values from the two images being compared.

The resulting differential image is binarized using a defect detection threshold value, and defect candidate points are extracted. The binarizing threshold value used to binarize the entire image can be, for example, a pre-set threshold value or a threshold value determined from the brightness of the inspected image or the like. Another example of how the threshold value can be set is to calculate threshold values for different coordinates or brightnesses in the image and then perform binarization using different threshold values for each point in the image.

The binarized image will contain erroneous information, but characteristics values extracted from the detected candidate points are used to find defects so that defect extraction can be as accurate as possible. A characteristics extraction module 274 calculates areas, coordinates, projected lengths, and the like of defect candidate points. Based on the determined characteristics values, a defect candidate point is evaluated to see if it is erroneous or not, and a defect 275 is detected.

Next, another embodiment using image processing that includes the processing of the two images to be compared will be described.

More specifically, brightness correction is actively applied to compare two images having different brightnesses.

Figure 29:
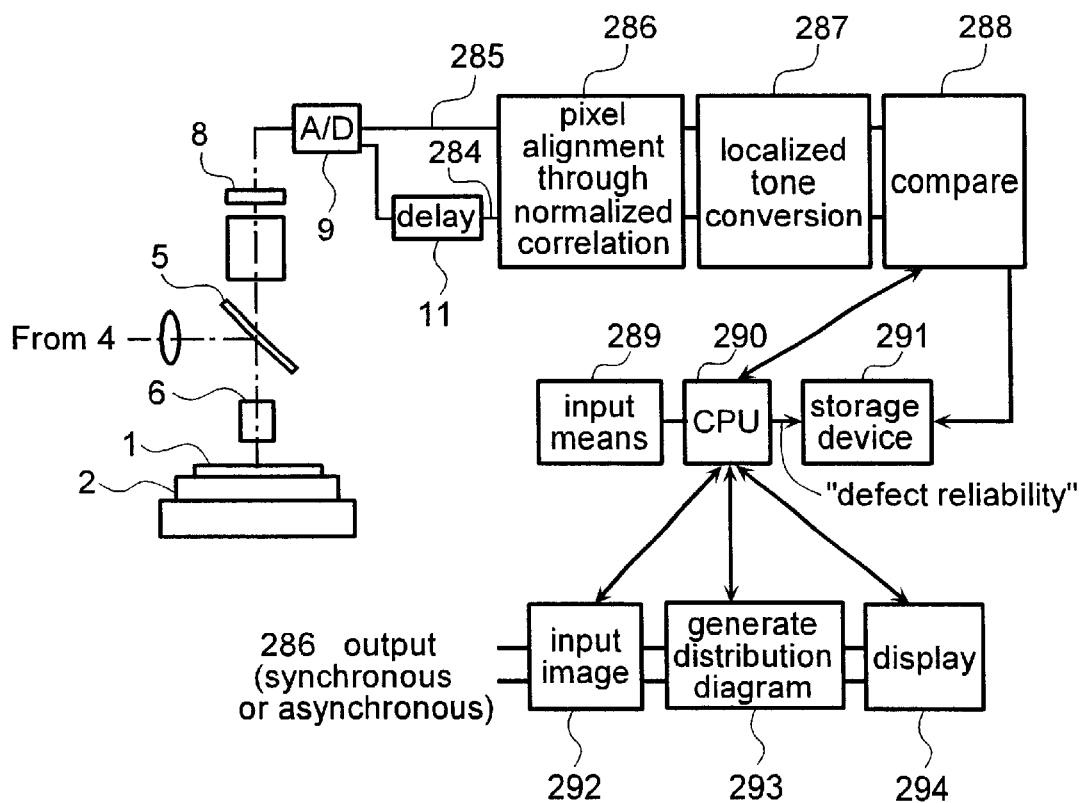
FIG. 29 is a schematic block diagram of a defect inspecting device according to the present invention.

In FIG. 29, the image sensor 8 (DUV-sensitive) outputs concentration image signals based on the brightness, i.e., concentration, of the light reflected from the semiconductor wafer 1, which provides the inspected pattern. The A/D converter 9 converts the concentration image signal obtained from the image sensor 8 into a digital image signal 285. The delay memory delays the concentration image signal. The semiconductor wafer 1 contains the pattern to be inspected. The stage 2, on which the semiconductor wafer 1 is mounted, can be moved in the X, Y, Z, and θ (rotation)

directions. The objective lens 6 is the lens for the semiconductor wafer 1. The half mirror 5 reflects the illumination light and illuminates the semiconductor wafer 1 through the objective lens 6 while also allowing light reflected from the semiconductor wafer 1 to pass through. The digital signal 285 is the signal converted from the concentration image signal by the A/D converter. In this manner, illumination light from a laser is reflected so that, for example, bright-field illumination is applied to the semiconductor wafer 1 through the objective lens 6. The scanning of the pupil of the objective lens 6 is performed using previously described methods.

The delay memory 11 can be a delay memory that stores the image signal 285 in units of repeated cells or at a pitch of multiple cells. Alternatively, the delay memory 11 can store the image signal 9 in units of repeated chips or at a pitch of multiple chips.

A signal 286 is used to align the digital image signal 285 and the delayed digital image signal 284. In this case, normalized correlation is performed to determine an offset that minimizes tone differences for individual image elements. One of the images is shifted based on this offset so that the two images can be aligned. The normalization is performed to reduce the influence of brightness differences between the images to be aligned.

The expressions below are used to move the stored image $g(x, y)$ relative to the detected image $f(x,y)$ and to determine a $(\Delta x, \Delta y)$ (where $(\Delta x, \Delta y;$ integers)) for which the correlation value is $R(\Delta x, \Delta y)$.

$$R(\Delta x, \Delta y) = \sum_{x=0}^{X-1}\sum_{y=0}^{Y-1} \frac{\{f(x, y) - \bar{f}\}\{g(x + \Delta x, \Delta y) - \bar{g}(\Delta x, \Delta y)\}}{\sqrt{f_\sigma \cdot g_\sigma(\Delta x, \Delta y)}} \quad \text{(expression 1)}$$

$$\bar{f} = \frac{1}{XY}\sum_{x=0}^{X-1}\sum_{y=0}^{Y-1} f(x, y) \quad \text{(expression 2)}$$

$$\bar{g}(\Delta x, \Delta y) = \frac{1}{XY}\sum_{x=0}^{X-1}\sum_{y=0}^{Y-1} g(x + \Delta x, y + \Delta y) \quad \text{(expression 3)}$$

$$f_\sigma = \sum_{x=0}^{X-1}\sum_{y=0}^{Y-1} \{f(x, y) - \bar{f}\}^2 \quad \text{(expression 4)}$$

$$g_\sigma(\Delta x, \Delta y) = \sum_{x=0}^{X-1}\sum_{y=0}^{Y-1} \{g(x + \Delta x, y + \Delta y) - \bar{g}(\Delta x, \Delta y)\}^2 \quad \text{(expression 5)}$$

The image is detected continuously by the image sensor, but the image is split up into smaller regions and alignment is performed for these regions. In the expressions above, the detected image has dimensions of X×Y image elements. The splitting up into small regions is performed to handle deformation in the image.

The size of these small regions is set up so that image deformation is at a negligible level.

While not indicated in the figure, the normalized correlation used to determine image offsets as described above does not need to be performed for all images. For example, an image can be divided along the longitudinal axis into K units. Out of the resulting small images (with X/K×Y image elements), it would be possible, then, to perform normalized correlation on only the small images with information. Whether or not information is present can be determined, for example, by applying differentiation to each small image to detect the presence of edges, and then selecting small images that have more edges. For example, if the image sensor is a multi-tap linear image sensor capable of parallel output, the output image from each tap would correspond to a small image. This idea is based on the fact that the images from the parallel output would have identical offsets. Furthermore, it would also be possible to apply normalized correlation on each of the small regions that have been split up, and then to determine the offset for regions with maximum correlation. The image sensor used here can be a DUV-sensitive TDI CCD image sensor, as described above, that is capable of parallel output.

A tone converter 287 converts the tones of image signals having different brightnesses so that the brightnesses of the two resulting images are uniform. In this case, the brightnesses are made uniform by applying gain and offset to individual image elements to perform linear conversion.

$$\sum_{x=-dx}^{dx}\sum_{y=-dy}^{dy} W(x, y, dx, dy) \cdot \{f(x, y) - a(x, y) \cdot g(x, y) - b(x, y)\}^2 \quad \text{(expression 6)}$$

$$W(x, y, dx, dy) = \max[1 - (f(x, y) - g(x + dx, y + dy))^2 / D^2, 0] \quad \text{(expression 7)}$$

$$a(x, y) = \frac{\left\{\sum_{x=-dx}^{dx}\sum_{y=-dy}^{dy}(W(x, y, dx, dy) \cdot g(x, y)) - \frac{1}{\sum_{x=-dx}^{dx}\sum_{y=-dy}^{dy} W(x, y, dx, dy)} \cdot \sum_{x=-dx}^{dx}\sum_{y=-dy}^{dy}\left[W(x, y, dx, dy) \cdot f(x, y) \cdot \sum_{x=-dx}^{dx}\sum_{y=-dy}^{dy} W(x, y, dx, dy) \cdot g(x, y)\right]\right\}}{\left\{\sum_{x=-dx}^{dx}\sum_{y=-dy}^{dy}(W(x, y, dx, dy) \cdot g(x, y) \cdot g(x, y)) - \frac{1}{\sum_{x=-dx}^{dx}\sum_{y=-dy}^{dy} W(x, y, dx, dy)} \cdot \sum_{x=-dx}^{dx}\sum_{y=-dy}^{dy}\left[W(x, y, dx, dy) \cdot g(x, y) \cdot \sum_{x=-dx}^{dx}\sum_{y=-dy}^{dy} W(x, y) \cdot g(x, y)\right]\right\}} \quad \text{(expression 8)}$$

$$b(x, y) = \frac{\left\{\sum_{x=-dx}^{dx}\sum_{y=-dy}^{dy}(W(x, y, dx, dy) \cdot f(x, y)) - a(x, y) \cdot \sum_{x=-dx}^{dx}\sum_{y=-dy}^{dy}(W(x, y, dx, dy) \cdot g(x, y))\right\}}{\sum_{x=-dx}^{dx}\sum_{y=-dy}^{dy}W(x, y, dx, dy)}$$

The resulting image signals are then compared by the comparator 288 and discrepancies are detected as defects.

Figure 31:
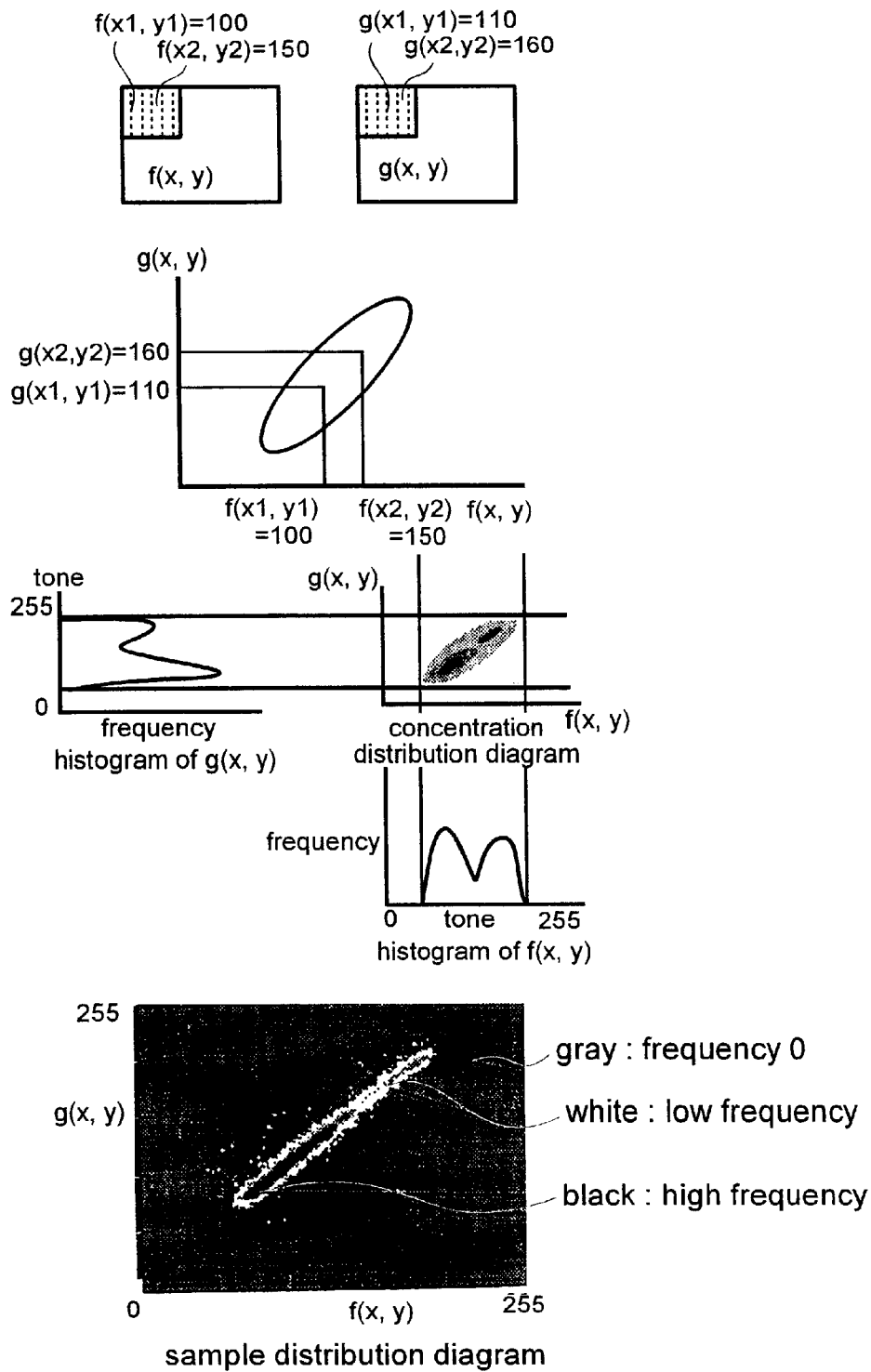
FIG. 31 is a flow diagram illustrating how scatter diagrams are generated according to the present invention.

The tone conversion for image signals can also be based on the scatter diagram shown in FIG. 31, to be described later. Linear approximation is applied to the data on the distribution graph, with the slope and intercept corresponding to a(x,y) and b(x,y) above. In the example shown in FIG. 31, gains and offsets are calculated based on an approximation line determined for individual areas centered around a focal point. Alternatively, linear approximation can be performed on the entire distribution graph. Another method is to generate multiple distribution graphs based on localized contrast and distribution patterns in the pattern. Then, linear approximation would be performed on the data on these distribution graphs. Alternatively, for each distribution graph, the data is divided into segment data parallel to a line with a 45-degree slope, i.e., the data would be grouped based on concentration differences, and then linear approximation would be performed on the divided data. The methods used to divide up contrast values, distribution values, and concentration differences are determined through tests.

After tone conversion is performed on the image elements using the method described above, a fixed sequence of operations are performed with an image processing pipeline. At the end of this process, defects and their characteristics are output.

The following is a description of the operations performed by an inspection device having the structure described above.

Referring to FIG. 29, the illuminating light is converged by the objective lens 6. The stage 2 is scanned along the X axis so that the inspection region of the semiconductor wafer 1 with the inspection pattern is moved at a uniform speed. The image sensor 8 detects brightness information (the concentration image signal) of the inspection pattern formed on the semiconductor wafer 1, i.e., the memory array and peripheral circuitry on the chip.

When scanning for one row is completed, the stage 2 is moved at a high speed along the Y axis to the next row and positioned. Thus, inspection is performed by repeating movements at a uniform speed and movements at a high speed. Step-and-repeat inspection can also be performed, of course. The A/D converter 9 converts the output (concentration image signal) into the digital image signal 285. This digital image signal 285 is a 10-bit signal. Of course, image signal can still be employed with about 6 bits, but a certain number of bits is required to detect fine defects.

In FIG. 29, input means 289, formed from a keyboard, disk, or the like, is used to enter coordinates for chip arrangement data or the like, based on design information, for the semiconductor wafer 1. Using these coordinates of the chip arrangement data or the like for the semiconductor wafer 1, the CPU 290 generates defect inspection data and stores it in the storage device 291. Defect reliability data, described later, expressing the reliability of the defect, is added to the defect inspection data and stored.

This defect inspection data, along with the defect reliability, can be displayed as needed on displaying means 294 formed from a display or the like. Alternatively, the information can be output using output means, such as a printer. Also, the defect inspection data and defect reliability can be communicated to other inspection devices, optical review devices, SEM review devices, defect categorization devices (a device that separates defects into categorizes using characteristics of defects. Various types such as ones that use neural networks are available), or the like. Of course, it would also be possible to display or output just the defect reliability information.

An image input module 292 receives two images to be compared. These images are used by a scatter diagram generating module 293 to generate a distribution graph. FIG. 31 shows how a scatter diagram is generated. The axes of the scatter diagram represent the brightnesses f(x, y) and g(x,y) of the two images to be compared. Instead of the brightnesses of the images to be compared, it would also be possible to have the axes represent localized contrast or localized average values. As shown in FIG. 31, the resulting scatter diagram is used to convert frequency to concentration, and the results are displayed. In this case, the display shows a frequency of 0 as gray, a low frequency as white, and a high frequency as black. Of course, it would also be possible to have the displayed scatter diagram indicate only the presence of data.

The scatter diagram of the image signal described above is used to calculate information either by using a function based on frequencies on the scatter diagram or positions on the scatter diagram or relative distance or by referring to a look-up table. The calculated information is added to the discrepancy information as defect reliability information, i.e., as a guide for whether a discrepancy is a defect, and is stored in the storage device 291.

A high frequency in the scatter diagram indicates that the point does not appear to be a defect. For example, in FIG. 31, the image elements associated with black data on the scatter diagram have high frequencies and there is a high probability that these are normal areas. The image elements associated with white data have low frequencies. The brightness indicates that there are not many of these areas and there is a high probability that these are defect areas. Thus, the frequency information can be considered an important parameter indicating defect reliability.

Similarly, with regard to positions on the scatter diagram, if the two images have the same brightnesses, the points will be distributed along a line sloped at 45 degrees. Thus, absolute positions on the scatter diagram are also an important parameter indicating defect reliability. In FIG. 31, image elements associated with data positioned away from the 45-degree line (not shown in the figure) also have low frequencies, and there is a high probability that these are defects.

Figure 32:
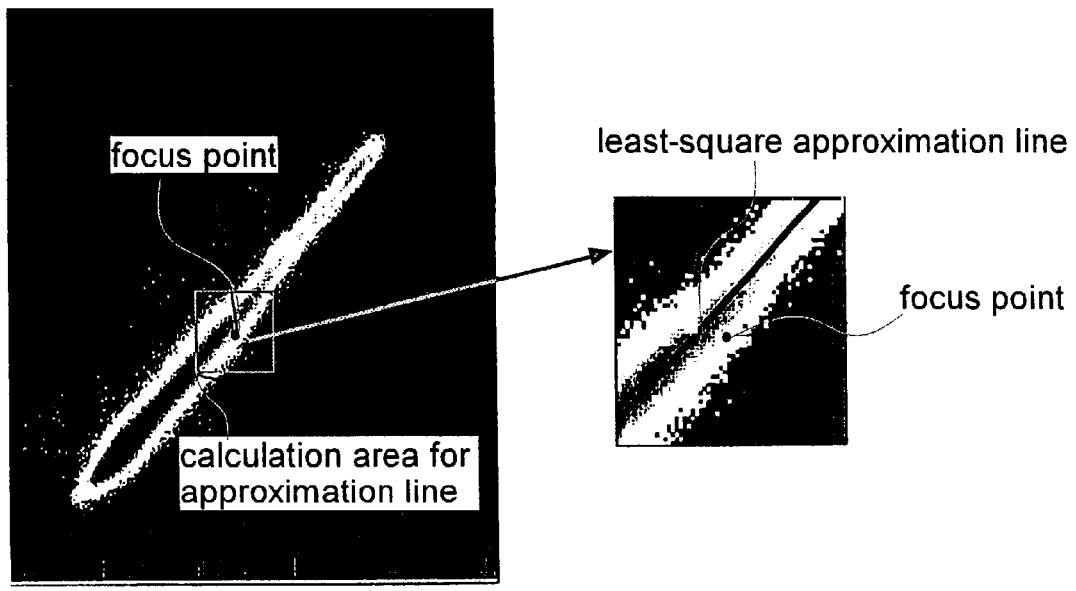
FIGS. 32(a) and 32(b) are photographs illustrating brightness correction according to the present invention.

With regard to relative distances on the scatter diagram, a scatter diagram based on the characteristics of each point is used to find a line with the least square error. The length of this line is then used. This is shown in FIGS. 32(a) and 32(b). As shown in the scatter diagram in FIG. 32(a), a scatter diagram is generated using the characteristic values of points, e.g., pattern contrast or localized distribution values. Then, an approximation line is determined for the data from each plane. Alternatively, the fact that frequency is a parameter indicating the reliability of a defect can be used. In this case, all points of the two images to be compared having a frequency of at least a fixed value are used. A line with the smallest least square error weighted using the multiple image elements in a predetermined area is calculated. The size of the area is locally variable according to the frequencies on the scatter diagram. For the method used to vary the size, it would be desirable to use a flexible system where frequencies are input and a look-up table is referenced to output an area size.

Using the approximation line obtained in this manner, brightness correction is performed, binarization using a threshold value is applied, and defects are output. Also, distances from the approximation line are determined and these distance values are output or displayed as indications of defect reliability. The smaller this distance is, the closer the position is to being normal. The larger the distance, the closer it is to being a defect. In FIG. 32(a), frequencies diminish as the distance from the approximation line increases, indicating that defect reliability is increasing. Regarding the use of points having a frequency of at least a fixed value, points with a frequency of 1 or less, for example, can be taken out of consideration in the linear approximation since they have a high probability of being defects. The localized tone converter 287 from FIG. 29 can also implement tone conversion using linear approximations determined using the method indicated in FIG. 32(a) for each image element.

Dispersion from a line in the overall image can be determined using, for example, the following expressions, where the line is Y=m f(x,y)+n.

$$Vr = \frac{1}{(2dx+1) \cdot (2dx+1) - 1} \qquad \text{(expression 10)}$$

$$\sum_{x=-dx}^{dx} \sum_{y=-dy}^{dy} (m \cdot f(x,y) + n - (m \cdot \overline{f(x,y)} + n))^2 =$$

$$\frac{1}{(2dx+1) \cdot (2dx+1) - 1}$$

$$\sum_{x=-dx}^{dx} \sum_{y=-dy}^{dy} (m \cdot (f(x,y) - \overline{f(x,y)}))^2$$

$$Ve = \frac{1}{(2dx+1) \cdot (2dx+1) - 2} \qquad \text{(expression 11)}$$

$$\sum_{x=-dx1}^{dx} \sum_{y=-dy}^{dy} (g(x,y) - (m \cdot f(x,y) + n))^2$$

This information can be used as a guide for the consistency of the images.

By using the information obtained from the scatter diagram in this manner, the reliability of the inconsistency information output from the inspection device can be evaluated.

In FIG. 29, a display module 294 displays the resulting scatter diagram. Input means 289 is used to enter threshold values and the like. For example, a threshold value for binarizing the absolute values from the differential image can be entered, and lines corresponding to the entered threshold value can be plotted on the scatter diagram. Looking at the scatter diagram, the appropriateness of the entered threshold value can be evaluated.

Figure 30:
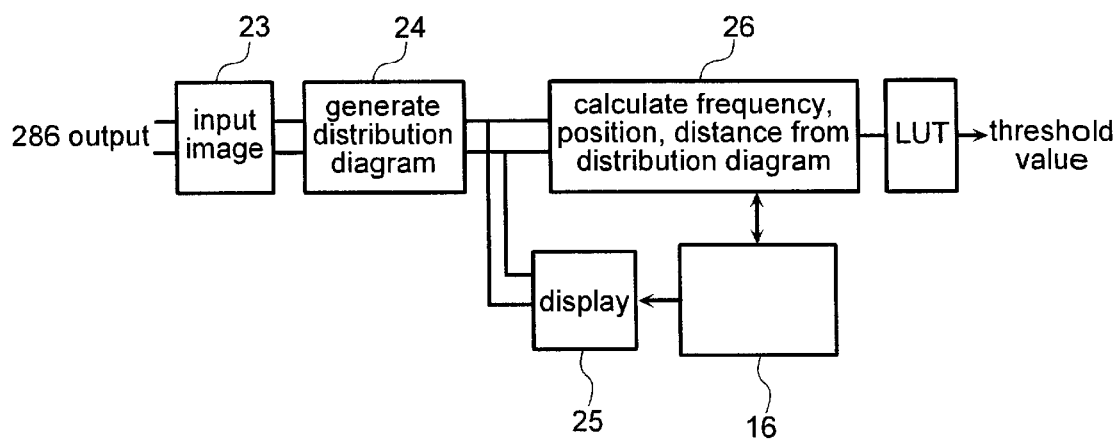
FIG. 30 is a schematic block diagram showing signal flows used to determine a threshold value according to the present invention.

Also, a threshold value suited for the image can be determined by referring to the displayed scatter diagram information. By choosing a threshold value based on the defect reliability described above, defect detection can be performed with greater reliability. For example, in a case where threshold values are determined adaptively by individual image elements, the threshold value can be determined based on frequencies in the scatter diagram. The conversion from frequency to threshold value is performed, as shown in FIG. 30, using a look-up table (LUT). The contents of the look-up table, i.e., the method used for conversion, are prepared before the inspection.

In FIG. 29, the images used for the scatter diagram are the two images to be compared and can, for example, be images that have been aligned on the image-element level. However, it would also be possible to input two images to the image input module 23 (FIG. 30) at any image processing step.

Figure 34:
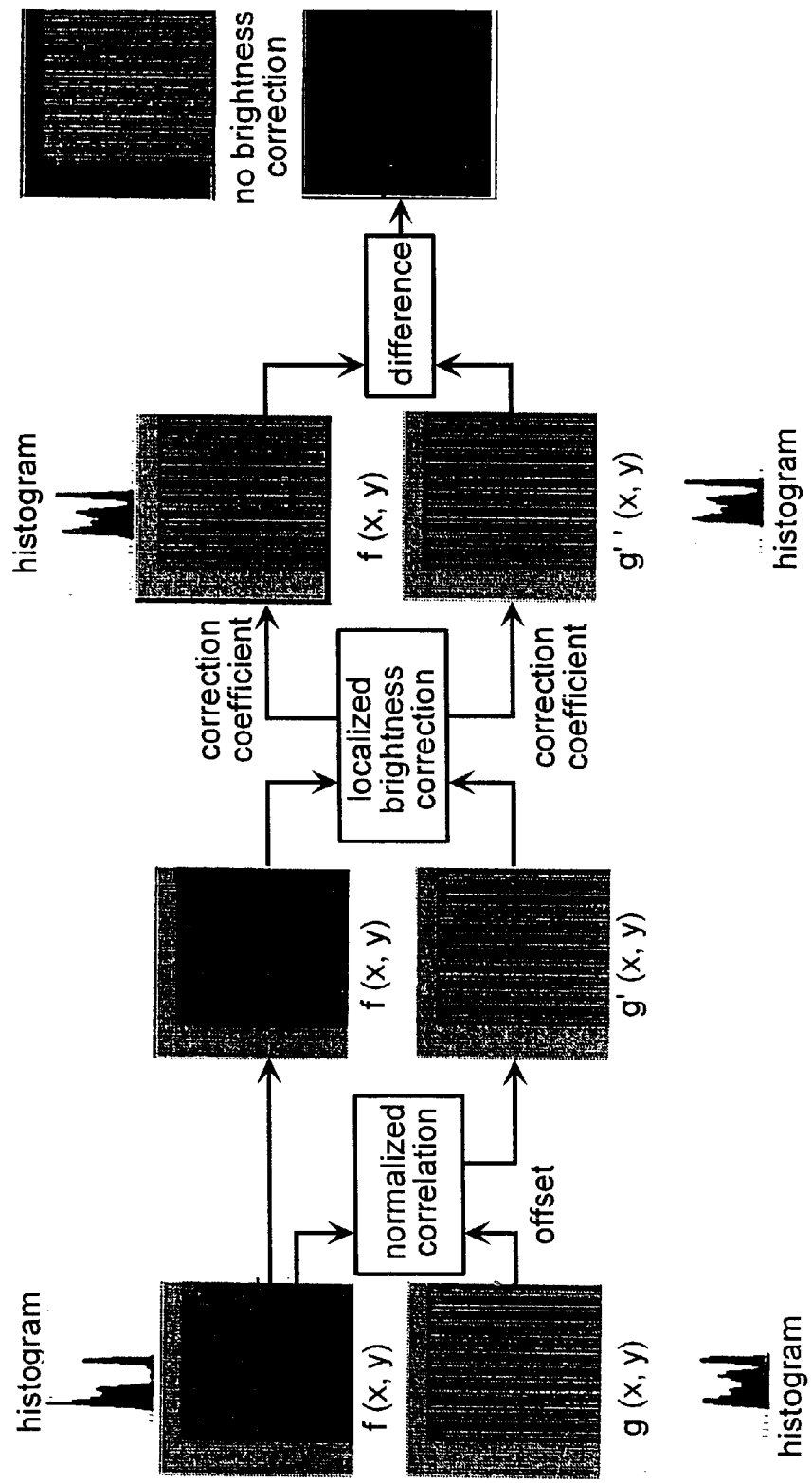
FIG. 34 is a diagram illustrating the flow of operations performed for defect evaluation according to the present invention.

FIG. 34 shows an example of how two images are processed using the system illustrated in FIG. 29. The inspected item is a pattern that has been polished with CMP (chemical-mechanical polishing) or the like. A pattern of lines and spaces are detected at the lower right of the image. The upper left area is an area with no patterns. An image histogram is also shown for each step. As the histograms show, the two brightnesses of the two images are not uniform at the initial step. First. normalized correlation is performed on the images to determine correlation values. The images are aligned at the image-element level by determining positions with correlations. Next, localized brightness correction, i.e., localized tone conversion, is performed for the two aligned images.

FIGS. 35(a) and 35(b) show scatter diagrams for the images. Since the brightnesses of the two images do not match when they have been aligned on the image-element level, the points are dispersed and do not lie on a 45-degree sloped line on the scatter diagram. However, with the localized tone conversion operation of the present invention (the system based on expressions 6 and 7), the points on the scatter diagram are close to the line, showing the effect of providing uniform brightness for the two images. The slopes and intercepts that are shown are the slopes and intercepts of line segments that have been fit to the scatter diagram data. The slope, which is a guideline for indicating consistency between the two images, is initially 0.705. However, after the localized brightness correction, i.e., the localized tone conversion, the slope is 0.986, indicating the improvement in consistency with regard to brightness. Furthermore, the Ve value described above, which indicates consistency between the two images, is initially 40.02 but becomes 8.598 after the localized brightness correction, i.e., the localized tone conversion, also indicating the improvement in consistency with regard to brightness.

In this example, values for the overall images are calculated based on the individual image elements that are being compared. However, it would also be possible to determine Ve and the like using the system shown in FIG. 31 where calculations are based on local areas on which tone conversion is performed.

This type of brightness correction is especially effective when the two images tb be compared have different brightnesses. Differences in brightness occur due to differences in film thickness between the corresponding patterns being compared. When the film thicknesses are different, a narrow illumination wavelength band will increase the brightness differences due to thin-film interference. In accordance with the present invention, polarization is controlled so that this influence is reduced, but residual differences in brightness are overcome with the correction described above. This allows even fine defects of 100 nm or less to be detected.

Figure 33:
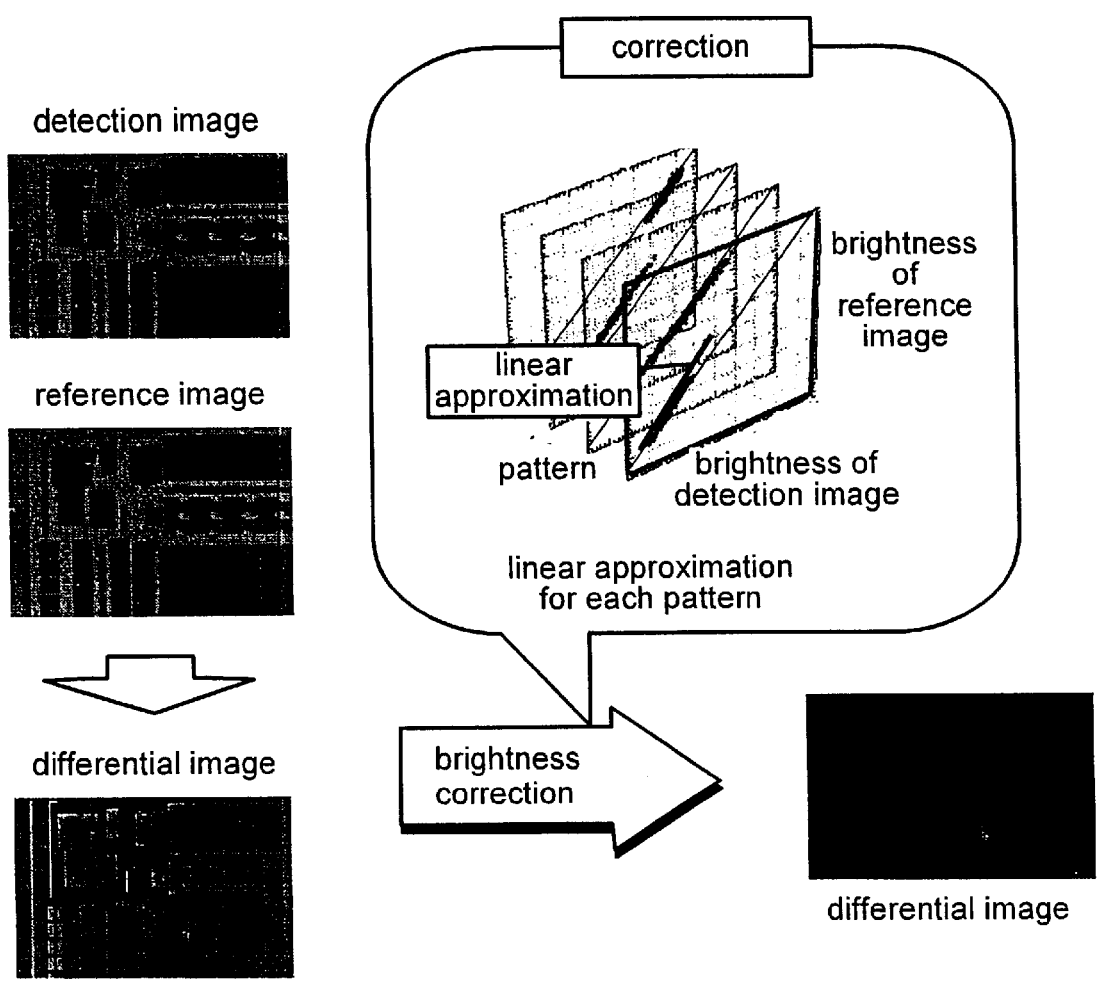
FIG. 33 is a diagram illustrating the flow of operations performed for brightness correction according to the present invention.

In the example shown in FIG. 33, the scatter diagrams, after localized brightness correction, are used to add defect reliability information to inconsistencies based on the procedure described above. In the scatter diagrams, the image elements dispersed in the periphery have a high defect reliability. A threshold value can be set using lines sloped 45 degrees on either side of the distributed data. Of course, defect reliability information can be extracted from scatter diagrams even at the stage where the images have been aligned at the image-element level. However, in such cases the threshold value cannot be set with a high degree of sensitivity since it must cover the distributed data.

Thus, it would be more desirable to use the scatter diagrams after localized brightness correction to determine threshold values.

The generation and display of scatter diagrams, the calculation of threshold values based on scatter diagrams, and the like are performed in synchronization with image detection for individual images or individual image elements in images. This provides high-sensitivity inspections. Also, the image processing operations are described above as an image processing pipeline, but it would also be possible to use a different type of system.

FIGS. 36(a)–36(c) show examples of defect output lists. The tone-converted images are compared by the comparator 288, and inconsistencies are output as these lists. In addition to numerical values indicating defect characteristics such as defect numbers, coordinates, lengths, and areas, defect reliability values are also added. Defect numbers are numbers assigned sequentially based on the order by which the inspected chip is scanned. The defect coordinates are for positions at which defects are defected in a coordinate system set up around an origin, alignment marks, and the like on the inspected chip. Defect lengths are the lengths of defects along the X axis and the Y axis. Of course, length along major axes and minor axes can also be calculated.

The units used for these values depend on the required precision, but can be, for example, in microns. Defect reliability values are information obtained from scatter diagrams as described above. For example, they can be based on frequency or distance from an approximation line of a defect image element using scatter diagrams as described above.

FIG. 36(a) is based on defect frequency in scatter diagrams. Lower frequencies indicate higher defect reliability. FIG. 36(b) is based on distance from approximation lines in scatter diagrams. Longer distances indicate higher defect reliability. FIG. 36(c) is based on defect positions in scatter diagrams. The further a point is from a line with a 45-degree slope, the higher the defect reliability. Of course, a defect image element can have multiple defect reliability values, e.g., based on frequency on scatter diagrams and based on distance from approximation lines. If a defect contains multiple image elements, statistical calculations are performed such as frequencies, average values, maximum values, and medians of the image elements. By adding reliability information to the inconsistency information, the criticality of defects can be calculated.

Figure 37:
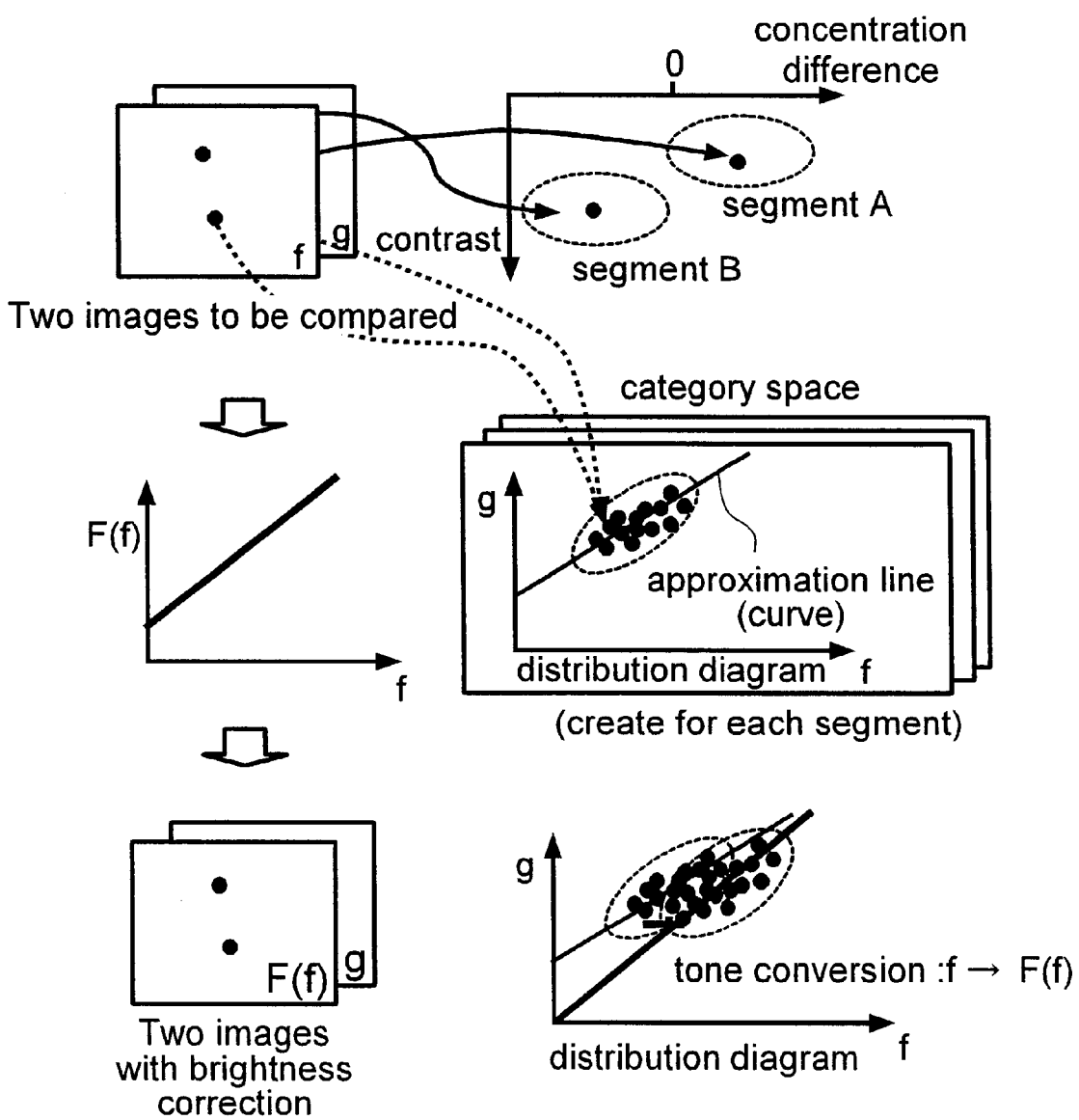
FIG. 37 is a flow diagram illustrating a method for determining a brightness conversion function according to the present invention.

A method for detecting defects while allowing for brightness differences in the two images to be compared will be described. As shown in FIG. 37, the brightnesses of the two images f and g are corrected to provide images f(f) and g. In this case, F(·) is a function for converting brightness. These are compared to detect defects through inconsistencies.

Next, a method for determining a brightness conversion function will be described.

First, each point in the image is mapped to "category space", as shown in FIG. 37. Category space is a space where the axes represent characteristics values. The characteristics values can, for example, be localized concentration differences between the two images (e.g., differences in brightness between an inspected image element and a corresponding image element), localized image contrast (e.g., maximum value—minimum value in a 2×2 image element area containing the inspected image element in image f), or the like. A segment is defined as a set of points in category space. FIG. 37 shows a segment A and a segment B. Dividing the points into segments in this manner is generally referred to as segmentation. Various segmentation methods have been developed. In this case, segmentation is performed simply based on frequency data in category space. Windows (e.g., 3×3) surrounding each data point are set up in category space, and a window size (e.g., 5×3) is determined so that the maximum frequency in the window is equal to the threshold value that was set up. A maximum window size is defined (e.g., 9×5). Data points within the same window are then considered to be part of the same segment. Points with high frequencies will belong to different categories, but belonging to different segments is not a problem since high frequencies indicate that the data-points are part of a normal (non-defective) pattern. Points with low frequencies will belong to a segment with a wide range (although this will correspond to the maximum range due to the upper limit on window size), thus increasing the defect probability.

Next, as shown in FIG. 37, two image scatter diagrams (in this case, brightness is used for the axes) are generated for each segment. The sets of points are approximated with a line. Approximation does not need to be linear and can also be higher-order approximations. e.g., polynomial. This linear approximation (curve) corresponds to the conversion function F(·) used to convert brightness (tone). Thus, an approximation line (curve) is determined for each segment.

Of the two images f, g to be compared, the brightness of f is converted using the approximation line (curve) for the segment to which each image element belongs, as shown in FIG. 37. This provides F(f). Since the data points in the narrow window described above belong to the same segment, the same approximation line is used, while the data from the adjacent window uses a different approximation line. Since these have higher frequencies, the distances of the data points from the approximation line will probably be shorter.

Conversely, with segments containing windows with low-frequency points, the scatter diagram data is dispersed and the distance of each data point from the approximation line is longer, indicating a higher defect probability. The segmentation method does not have to be the method described above and other methods can be used as long as they do not depart from the spirit of the invention. Also, when performing linear approximation, eliminating low-frequency data from consideration can prevent the approximation accuracy from being reduced due to a small number of data points.

The resulting F(f) and g images serve as the brightness-corrected images to be compared. These are compared to detect discrepancies. By performing brightness correction, the binarization threshold value for the differences between the two images can be set to a low value, thus improving defect detection sensitivity.

The two images f, g to be compared are aligned to each other beforehand. Also, brightness correction was applied only to one image in this case, but it would also be possible to apply correction to both images.

The criticality of a defect refers to the degree of criticality that a defect has on the inspected pattern and can be determined, for example, by the size and coordinates (area) of the defect. Given defects having the same size, the defect on a pattern with smaller dimensions will have a higher criticality. By using this type of criticality evaluation together with defect reliability information, the evaluation of criticality can be performed with higher accuracy, thus making process diagnosis for the inspected pattern more appropriate.

In the image detection operations described above, each image element is processed at 10 MHz or faster. This allows a wafer with a diameter on the order of 200 mm to be processed at a speed corresponding to a throughput of 3 pieces per hour with detection including defects of 100 nm and less. Thus, useful inspection information can be output at an appropriate pace in a semiconductor production line. Also, defect inspection can be performed on wafers with diameters on the order of 300 mm with the same throughput as wafers having diameters on the order of 200 mm.

With the present invention as described above, high-tuminance illumination is provided and high-resolution images can be formed in short periods. As a result, a high-speed, high-sensitivity inspection device can be provided. The positions and dimensions of detected pattern defects are output.

With the embodiments described above, illumination is provided with shortwave lengths required for high-resolution imaging. A laser light-source, which is effective for this type of application, is used, and image quality that is equivalent or higher than that of standard discharge tube illumination is provided. This results in high sensitivity and high speeds and allows fine defects to be detected with high sensitivity.

The invention may be embodied in other specific forms without departing from the spirit or essential characteristics thereof. The present embodiment is therefor to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. An apparatus for inspecting defects in a patterned specimen, comprising:
    laser light source means for emitting a laser;
    coherency reducing means for reducing coherency of said laser emitted from said laser light source means;
    illuminating weans for illuminating a specimen with a laser of which a coherency thereof is reduced by said coherency reducing means;
    image detecting weans for detecting an image of said specimen illuminated by said laser from said illuminating means; and
    defect detecting means for detecting pattern defects formed on said specimen based on information relating to said image of said specimen detected by said image detecting means;
    wherein said illuminating means includes an objective lens module, a focusing optical system which focuses said laser onto a pupil of said objective lens, and a scanning module which scans said laser on the pupil of said objective lens.

2. An apparatus according to the claim 1, wherein said scanning module scans said laser on said pupil using a mirror.

3. An apparatus according to the claim 1, wherein said image detecting means detects images with a storage-type image sensor, and said scanning module effects scanning of the laser on the pupil in synchronism with a storage time of the image sensor.

4. An apparatus according to the claim 1, wherein said defect detecting means includes a storage module storing a reference image signal and a pattern detection module detecting defects in patterns formed on said specimen by comparing an image signal of said specimen output from said image detecting means with a reference image signal stored in said storage module.

5. An apparatus for inspecting defects in a patterned specimen, comprising:
    a laser light source which emits a UV laser;
    a coherency reducer which reduces coherency of said UV laser emitted from said laser light source;
    an illuminator which illuminates a specimen with said UV laser of which a coherency thereof is reduced by said coherency reducer;
    a polarizing means which adjusts polarization states of said UV laser;
    an image detector which detects an image of said specimen formed by diffracted light by the illumination of said UV laser from said illuminator and in which a polarization condition of said diffracted light is adjusted by said polarizing means; and
    a defect detector which detects defects of a pattern formed on said specimen based on information relating to said image of said specimen detected by said image detector.

6. An apparatus according to the claim 5, wherein said polarizing means includes a quarter-wave plate or a half-wave plate and a quarter-wave plate disposed in an optical path connecting said laser light source and said specimen, and an analyzer disposed in an optical path connecting said specimen and said image detector.

7. An apparatus according to the claim 6, wherein at least one of said half-wave plate, said quarter-wave plate, and said analyzer is rotatable.

8. An apparatus according to the claim 6, wherein said image detecting means includes time delay integration (TDI) image sensor means that is sensitive to UV light.

9. An apparatus according to the claim 8, wherein said TDI image sensor is an anti-blooming TDI sensor.

10. An apparatus according to the claim 8, wherein said TDI image sensor is at back-illumination TDI sensor.

11. An apparatus according to the claim 5, wherein said defect inspecting means includes a storage module storing a reference signal and a defect detection module detecting defects in patterns formed on said specimen by comparing an image signal of said specimen output from said image detecting means with a reference image signal stored in said storage module.

12. An apparatus according to the claim 5, wherein said coherency reducer includes an optical path section formed from a plurality of glass rod lenses or a plurality of cylindrical lens arrays and a focus lens;

wherein said laser emitted from said laser light source means is passed through said optical path section formed from said plurality of glass rod lenses or said plurality of cylindrical lens arrays and said focus lens and exits from another end toward an objective lens of said illuminator; and wherein said laser is scanned on a pupil of said objective lens.

13. An apparatus according to the claim 5, wherein said defect detecting means outputs information relating to positions and dimensions of detected defects in said pattern.

14. An apparatus for inspecting a defect, comprising:

a laser light source which emits a laser;

a coherency reducer which reduces coherency of said laser emitted by said laser light source means;

an illuminator which illuminates a specimen with said laser of which a coherency thereof is reduced by said coherency reducer;

an analyzer which adjusts polarization states of light diffracted from the specimen illuminated by the illuminator;

an image detector which detects an image of said specimen formed by diffracted light from said specimen and passed through said analyzer; and an image processor which processes an image of said specimen detected by said image detector;

wherein said apparatus processes said-specimen having a diameter on the order of 200 mm at a speed corresponding to a throughput of three units per hour, and detects defects in the order of 100 nm on said patterns formed on said specimen.

15. A method of inspecting a defect of a pattern, comprising the steps of:

illuminating with a UV laser a specimen on which a pattern is formed;

imaging said specimen illuminated with said UV laser; and detecting defects on said pattern by comparing an image of said specimen obtained by said imaging step with a previously stored reference image;

wherein said image of said specimen obtained by said imaging step is formed by light from said specimen of which a polarization state thereof is adjusted.

16. A method of inspecting a defect of a pattern, comprising the steps of:

focussing and scanning a UV laser on a pupil of an objective lens;

illuminating a specimen on which a pattern is formed with said focused and scanned UV laser;

imaging said specimen illuminated by said UV laser; and detecting defects on said pattern by comparing an image of said specimen obtained by said imaging step with a previously stored reference image.

17. A method of inspecting a defect, comprising the steps of:

illuminating a specimen on which a pattern is formed with UV light;

imaging said specimen illuminated by UV light;

correcting a difference in brightness between an image of said specimen obtained by said imaging step and a previously stored reference image so that brightnesses are roughly identical; and detecting defects on said pattern by comparing said image of said specimen and said reference image which have been corrected for brightness.

18. A method according to the claim 17, wherein said UV light illuminating said specimen is emitted from a laser light source and is a UV light in which laser coherence has been reduced.

19. A method of inspecting a defect, comprising the steps of:

reducing coherence of a laser emitted from a laser light source;

illuminating a surface of a specimen on which a pattern is forced via an objective lens using said laser with reduced coherence while varying the direction of illumination over time;

imaging said specimen illuminated by said laser; and detecting defects on said pattern by comparing paid image of said specimen obtained in said imaging step and a previously stored reference image;

wherein said image of said specimen obtained in said imaging step is formed by light from said specimen of which a polarization state thereof is adjusted.

20. A method according to the claim 19, wherein said image of said specimen obtained in said imaging step is an image obtained by taking an image of said specimen illuminated by said laser and changing the polarization state using an analyzer.

21. A method of inspecting a defect, comprising the steps of:

illuminating a surface of a specimen through an object lens using UV light;

obtaining an image signal with an image sensor by imaging said surface of said specimen illuminated by said UV light;

detecting defects of no greater than 100 nm on said specimen by processing said image signal; and outputting information relating to positions on said specimen of detected defects of 100 nm and less;

wherein in the step of illuminating, said UV light is scanned on a pupil of said object lens in synchronism with operation of said image sensor.

22. A method according to the claim 21, wherein said UV light illuminating said surface of said specimen is emitted from a laser light source and is a UV light with reduced laser coherence.

23. A method according to the claim 21, wherein said specimen is imaged using a time delay integration (TDI) image sensor.

24. A method according to the claim 21, wherein said specimen is imaged using an anti-blooming time delay integration (TDI) image sensor.

25. A method according to the claim 21, wherein said specimen is imaged using a back-illumination type time delay integration (TDI) image sensor.

26. A method according to the claim 21, wherein information relating to positions and dimensions of said detected defects are output.

27. A method according to the claim 21, wherein said UV light illuminates said specimen through an objective lens having an NA of at least 0.75.

28. A method according to the claim 21, wherein an image signal is obtained by imaging, in synchronization with movements of said specimen, said surface of said specimen using a time delay integration image sensor, said image signal being compared to a previously stored reference image signal to detect defects on said specimen.

29. A method of inspecting a defect, comprising the steps of:

illuminating UV light on a wafer with a diameter that is at least on the order of 200 mm;

detecting an image of said wafer by imaging said wafer illuminated by said UV light;

detecting defects of no greater than 100 mm on patterns formed on said wafer by processing said detected images of said wafer illuminated by said UV light, said detection being performed at a throughput of at least three wafers with said 200 mm diameter per hour;

wherein in the step of detecting, said image is detected by at least one of (a) a back-illumination type time delay integration (TDI) image sensor, (b) a TDI image sensor having anti-blooming characteristics, and (c) a TDI image sensor coated with an organic thin-film.

30. An apparatus according to claim 2, wherein said mirror is a galvano-mirror.

* * * * *